(12) United States Patent
Fujii et al.

(10) Patent No.: US 7,833,722 B2
(45) Date of Patent: Nov. 16, 2010

(54) LIGANDS FOR G PROTEIN-COUPLED RECEPTOR PROTEIN AND USE THEREOF

(75) Inventors: Ryo Fujii, Osaka (JP); Masataka Harada, Osaka (JP); Shuji Hinuma, Osaka (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 779 days.

(21) Appl. No.: 11/587,631

(22) PCT Filed: Apr. 26, 2005

(86) PCT No.: PCT/JP2005/008403

§ 371 (c)(1),
(2), (4) Date: Oct. 26, 2006

(87) PCT Pub. No.: WO2005/103291

PCT Pub. Date: Nov. 3, 2005

(65) Prior Publication Data

US 2008/0248041 A1    Oct. 9, 2008

(30) Foreign Application Priority Data

Apr. 27, 2004    (JP) .............................. 2004-131726

(51) Int. Cl.
*G01N 33/53* (2006.01)
(52) U.S. Cl. ......................... 435/7.1; 435/7.2
(58) Field of Classification Search ........................ None
See application file for complete search history.

(56) References Cited

U.S. PATENT DOCUMENTS 6,555,339 B1 *   4/2003   Liaw et al. .................. 435/69.1
2004/0176344 A1   9/2004   Rooney

FOREIGN PATENT DOCUMENTS

| GB | 2 360 586 A | 9/2001 |
|---|---|---|
| WO | WO-94/12635 | 6/1994 |
| WO | WO-01/68842 A2 | 9/2001 |
| WO | WO-03/025138 A2 | 3/2003 |
| WO | WO-03/071272 A1 | 8/2003 |

OTHER PUBLICATIONS

Carol J. Raport et al.; "New Members of the Chemokine Receptor Gene Family", Journal of Leukocyte Biology, vol. 59, pp. 18-28, Jan. 1996.
Rainer Blasius et al., "A Novel Orphan G Protein-Coupled Receptor Primarily Expressed in the Brain is Localized on Human Chromosonal Band 2q21"; Journal of Neurochemistry, vol. 70, No. 4, pp. 1357-1365 (1998).
Charles De Smet et al.; "A Novel Seven Transmembrane Receptor Induced During the Early Steps of Astrocyte Differentiation Identified by Differential Expression;" Journal of Neurochemistry, 81, pp. 575-588 (2002).
Walter E. Muller; δ-Aminolevulinic Acid: Influences of Synaptic GABA Receptor Binding May Explain CNS Symptoms of Porphyria; Ann Neurol. 2: pp. 340-342 (1977).
Martin J. Warren et al.; "Lead Poisoning, Haem Synthesis and 5-aminolaevulinic Acid Dehydratase"; TIBS 23, pp. 217-221 (Jun. 1998).
Steen J. Madsen, et al.: "Repetitive 5-aminolevulinic acid-mediated photodynamic therapy on human glioma spheroids," Journal of Neuro-Oncology 62: 243-250, 2003.

* cited by examiner

*Primary Examiner*—Marianne P Allen

(57) ABSTRACT

The present invention provides a method of screening an agonist/antagonist of a G protein-coupled receptor protein comprising the same or substantially the same amino acid sequence as the amino acid sequence represented by SEQ ID NO: 1, or a salt thereof, which comprises using the receptor protein or its salt and a ligand or its salt; and so on. The screening method of the present invention is useful for screening an agent for the prevention/treatment of nervous system diseases or neuropathic pains.

3 Claims, 3 Drawing Sheets

SEQUENCE LISTING

```
<160> NUMBER OF SEQ ID NOS: 5

<210> SEQ ID NO 1
<211> LENGTH: 339
<212> TYPE: PRT
<213> ORGANISM: Homo sapiens

<400> SEQUENCE: 1

Met Asn Gly Leu Glu Val Ala Pro Pro Gly Leu Ile Thr Asn Phe Ser
1               5                   10                  15

Leu Ala Thr Ala Glu Gln Cys Gly Gln Glu Thr Pro Leu Glu Asn Met
            20                  25                  30

Leu Phe Ala Ser Phe Tyr Leu Leu Asp Phe Ile Leu Ala Leu Val Gly
        35                  40                  45

Asn Thr Leu Ala Leu Trp Leu Phe Ile Arg Asp His Lys Ser Gly Thr
    50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Ala Cys Arg Leu Thr Gly Phe Leu Phe Tyr
            100                 105                 110

Leu Asn Met Tyr Ala Ser Ile Tyr Phe Leu Thr Cys Ile Ser Ala Asp
        115                 120                 125

Arg Phe Leu Ala Ile Val His Pro Val Lys Ser Leu Lys Leu Arg Arg
    130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Val Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Leu Arg
    210                 215                 220
```

| | | | | | | | | | | | |
|---|---|---|---|---|---|---|---|---|---|---|---|
|Val|Glu|Lys|Arg|Leu|Lys|Thr|Lys|Ala|Val|Arg|Met|Ile|Ala|Ile|Val|
|225| | | |230| | | |235| | | |240| | | |

| | | | | | | | | | | | |
|---|---|---|---|---|---|---|---|---|---|---|---|
|Leu|Ala|Ile|Phe|Leu|Val|Cys|Phe|Val|Pro|Tyr|His|Val|Asn|Arg|Ser|
| | | | |245| | | |250| | | |255| | | |

| | | | | | | | | | | | |
|---|---|---|---|---|---|---|---|---|---|---|---|
|Val|Tyr|Val|Leu|His|Tyr|Arg|Ser|His|Gly|Ala|Ser|Cys|Ala|Thr|Gln|
| | | |260| | | |265| | | |270| | | | |

| | | | | | | | | | | | |
|---|---|---|---|---|---|---|---|---|---|---|---|
|Arg|Ile|Leu|Ala|Leu|Ala|Asn|Arg|Ile|Thr|Ser|Cys|Leu|Thr|Ser|Leu|
| |275| | | |280| | | |285| | | | | | |

| | | | | | | | | | | | |
|---|---|---|---|---|---|---|---|---|---|---|---|
|Asn|Gly|Ala|Leu|Asp|Pro|Ile|Met|Tyr|Phe|Phe|Val|Ala|Glu|Lys|Phe|
|290| | | |295| | | |300| | | | | | | |

| | | | | | | | | | | | |
|---|---|---|---|---|---|---|---|---|---|---|---|
|Arg|His|Ala|Leu|Cys|Asn|Leu|Leu|Cys|Gly|Lys|Arg|Leu|Lys|Gly|Pro|
|305| | | |310| | | |315| | | |320| | | |

| | | | | | | | | | | | |
|---|---|---|---|---|---|---|---|---|---|---|---|
|Pro|Pro|Ser|Phe|Glu|Gly|Lys|Thr|Asn|Glu|Ser|Ser|Leu|Ser|Ala|Lys|
| | | |325| | | |330| | | |335| | | | |

Ser Glu Leu

```
<210> SEQ ID NO 2
<211> LENGTH: 1020
<212> TYPE: DNA
<213> ORGANISM: Homo sapiens
<220> FEATURE:
<221> NAME/KEY: misc_feature
<222> LOCATION: (330)..(330)
<223> OTHER INFORMATION: n is a, c, g, or t

<400> SEQUENCE: 2
```

| | | | | | |
|---|---|---|---|---|---|
|atgaatggcc|ttgaagtggc|tcccccaggt|ctgatcacca|acttctccct|ggccacggca|60|
|gagcaatgtg|gccaggagac|gccactggag|aacatgctgt|tcgcctcctt|ctaccttctg|120|
|gattttatcc|tggctttagt|tggcaatacc|ctggctctgt|ggcttttcat|ccgagaccac|180|
|aagtccggga|ccccggccaa|cgtgttcctg|atgcatctgg|ccgtggccga|cttgtcgtgc|240|
|gtgctggtcc|tgcccacccg|cctggtctac|cacttctctg|ggaaccactg|gccatttggg|300|
|gaaatcgcat|gccgtctcac|cggcttcctn|ttctacctca|acatgtacgc|cagcatctac|360|
|ttcctcacct|gcatcagcgc|cgaccgtttc|ctggccattg|tgcacccggt|caagtccctc|420|
|aagctccgca|ggcccctcta|cgcacacctg|gcctgtgcct|tcctgtgggt|ggtggtggct|480|
|gtggccatgg|ccccgctgct|ggtgagccca|cagaccgtgc|agaccaacca|cacggtggtc|540|
|tgcctgcagc|tgtaccggga|gaaggcctcc|accatgccc|tggtgtccct|ggcagtggcc|600|
|ttcaccttcc|cgttcatcac|cacggtcacc|tgctacctgc|tgatcatccg|cagcctgcgg|660|
|cagggcctgc|gtgtggagaa|gcgcctcaag|accaaggcag|tgcgcatgat|cgccatagtg|720|
|ctggccatct|tcctggtctg|cttcgtgccc|taccacgtca|accgctccgt|ctacgtgctg|780|
|cactaccgca|gccatggggc|tcctgcgcc|acccagcgca|tcctggccct|ggcaaaccgc|840|
|atcacctcct|gcctcaccag|cctcaacggg|gcactcgacc|ccatcatgta|tttcttcgtg|900|
|gctgagaagt|tccgccacgc|cctgtgcaac|ttgctctgtg|gcaaaggct|caagggcccg|960|
|cccccagct|tcgaagggaa|aaccaacgag|agctcgctga|gtgccaagtc|agagctgtga|1020|

```
<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
```

-continued

```
gtctcaccgg cttcctcttc t                                          21

<210> SEQ ID NO 4
<211> LENGTH: 17
<212> TYPE: DNA
<213> ORGANISM: Artificial
<220> FEATURE:
<223> OTHER INFORMATION: Primer

<400> SEQUENCE: 4
aaacggtcgg cgctgat                                               17

<210> SEQ ID NO 5
<211> LENGTH: 30
<212> TYPE: DNA
<213> ORGANISM: Artificial
<220> FEATURE:
<223> OTHER INFORMATION: Probe

<400> SEQUENCE: 5
cctcaacatg tacgccagca tctacttcct                                 30
```

LIGANDS FOR G PROTEIN-COUPLED RECEPTOR PROTEIN AND USE THEREOF

TECHNICAL FIELD

The present invention relates to novel ligands for a G protein-coupled receptor protein and use thereof.

BACKGROUND ART

Physiologically active substances such as various hormones, neurotransmitters, etc. regulate the biological function via specific receptor proteins present on cell membranes. Many of these receptor proteins are coupled with a guanine nucleotide-binding protein (hereinafter sometimes simply referred to as G protein) and mediate the intracellular signal transduction via activation of G protein. These receptor proteins possess the common structure containing seven transmembrane domains and are thus collectively referred to as G protein-coupled receptor proteins (GPCR) or seven-transmembrane receptor proteins (7TMR).

G protein-coupled receptor proteins are present on the cell surface of each functional cell and organ in the body, and play important physiological roles as the target of the molecules that regulate the functions of these cells and organs, e.g., hormones, neurotransmitters, physiologically active substances and the like. Receptors transmit signals to cells via binding with physiologically active substances, and the signals induce various reactions such as activation and inhibition of the cells.

To clarify the relationship between substances that regulate complex biological functions in various cells and organs in the body, and their specific receptor proteins, in particular, G protein-coupled receptor proteins would elucidate the functional mechanisms in various cells and organs in the body to provide a very important means for development of drugs closely associated with these functions.

For example, in various organs in the body, their physiological functions are controlled through regulation by many hormones, hormone-like substances, neurotransmitters or physiologically active substances. In particular, physiologically active substances are found in numerous sites of the body and regulate the physiological functions through their corresponding receptor proteins. Many unknown hormones, neurotransmitters or many other physiologically active substances still exist in the body and, as to their receptor proteins, many of these proteins have not yet been reported. In addition, it is still unknown if there are subtypes of known receptor proteins.

It is a very important means for development of drugs to clarify the relationship between substances that regulate complex functions in vivo and their specific receptor proteins. Furthermore, for efficient screening of agonists and antagonists to receptor proteins in development of drugs, it is required to clarify functions of genes for these receptor proteins expressed in vivo and express the genes in an appropriate expression system.

In these receptor proteins, receptor proteins in which the corresponding ligands including agonists and antagonists are yet unidentified are referred to as orphan receptor proteins. GPR17 is known as one of the orphan G protein-coupled receptor proteins. WO 94/12635 discloses only sequence information of GPR17. GB 2360586 discloses this protein as a leukotriene receptor but has no description of expression distribution therein and merely mentions that other known leukotriene receptor is expressed in the lung and thus available for the treatment or prevention of immune diseases such as COPD, allergic rhinitis, AIDS, rheumatism, psoriasis, atopic dermatitis, etc., and cardiovascular diseases. WO 2003/025138 describes GPR17 as one of genes whose expression is changed in cancer. WO 2003/07127 discloses a ligand screening assay using an orphan GPCR-GFP fusion protein, in which a GPR17-GFP fusion sequence is shown. In J. Neurochem., 70, 1357-1365 (1998), a variant with a 28-amino acid N-terminal extension is reported. This gene is cloned from human hippocampus and shown to be expressed in the brain. In J. Neurochem., 81, 575-588 (2002), rat GPR17 is reported to be expressed in the oligodendrocyte.

On the other hand, it is known in Acta Haematol., 1958, 19 (6): 321-326 that 5-aminolevulinic acid is a hem protein precursor, and the urine level of 5-aminolevulinic acid increases in the patient with lead poisoning to cause severe neuropathy as a result. It is described in Trends Biochem. Sci., 1998, 23, 217-221 that 5-aminolevulinic acid and porphobilinogen take part in lead poisoning.

DISCLOSURE OF THE INVENTION

Heretofore, substances that inhibit the binding of G protein-coupled receptor proteins to physiologically active substances (i.e., ligands) and substances that bind and induce signal transduction similar to those physiologically active substances (i.e., ligands) have been utilized for pharmaceuticals as antagonists and agonists specific to these receptor proteins that regulate the biological functions. Therefore, newly finding G protein-coupled receptor proteins that can be targeted for pharmaceutical development as well as that are important in physiological phenomenon in vivo, and cloning their genes (e.g., cDNAs) are very important means in search for new G protein-coupled receptor protein-specific ligands, agonists and antagonists.

However, all of these G protein-coupled receptors are not discovered; there are a lot of unknown G protein-coupled receptors and a lot of so-called orphan receptors such as the GPR17 described above even at this point of time. Thus, search of novel G protein-coupled receptors and elucidation of their functions are eagerly awaited.

G protein-coupled receptors are useful in search for a novel physiological active substance (i.e., ligand) using the signal transduction activity as an indicator and in search for agonists and antagonists of the receptors. On the other hand, even though no physiological ligand is found, agonists and antagonists of the receptors may be prepared by analyzing the physiological action of the receptors through inactivation experiment of the receptors (knockout animal). Ligands, agonists or antagonists, etc. for these receptors are expected to be utilized as preventive and/or therapeutic agents and diagnostic agents for diseases associated with dysfunction of the G protein-coupled receptors.

Furthermore, suppression or progression of functions of G protein-coupled receptor in vivo due to genetic aberration of the receptor often causes some disorders. In this case, not only administration of antagonists or agonists of the receptor, but gene therapy is also applicable by transfer of genes for the receptor into the body (or some particular organs) or by introduction of the antisense nucleic acid of genes for the receptor. In this case, information on the base sequence of the receptor is essentially required for investigating deletion or mutation on the gene. The genes for the receptor are also applicable as preventive and/or therapeutic agent or diagnostic agents for diseases associated with dysfunction of the receptor.

Specifically, an object of the present invention is to determine ligands for GPR17 and provide the use of GPR17 and its ligands. In other words, the objects of the present invention are providing a method of screening a compound (antagonist or agonist) or its salt that alters the binding property of a ligand to GPR17; a kit for the screening; a compound (antagonist or agonist) or its salt that alters the binding property of the ligand to GPR17, which is obtained by the screening method or screening kit; a medicament comprising the compound (antagonist or agonist) or its salt that alters the binding property of the ligand to GPR17.

In order to solve the foregoing problems described above, the present inventors have made extensive studies and as a result, found that 5-aminolevulinic acid and porphobilinogen are ligands for GPR17, using a screening method for the ligands disclosed in Japanese Patent Application No. 2003-393056, which requires no specific cell line. Based on these findings, the inventors have made further investigations and come to accomplish the present invention.

That is, the present invention provides the following features, and so on.

[1] A method of screening a compound or its salt that alters the binding property of a G protein-coupled receptor protein comprising the same or substantially the same amino acid sequence as the amino acid sequence represented by SEQ ID NO: 1, or a salt thereof, to a ligand or a salt thereof, which comprises using (1) said receptor protein, a partial peptide thereof, or a salt thereof and (2) said ligand or a salt thereof.

[2] The screening method according to [1] above, wherein the ligand is 5-aminolevulinic acid.

[3] The screening method according to [1] above, wherein the ligand is porphobilinogen.

[4] A method of screening an agonist or antagonist of a G protein-coupled receptor protein comprising the same or substantially the same amino acid sequence as the amino acid sequence represented by SEQ ID NO: 1, or a salt thereof, which comprises using (1) said receptor protein, a partial peptide thereof, or a salt thereof and (2) a compound or its salt that alters the binding property of said ligand or a salt thereof to said receptor protein or a salt thereof.

[5] The screening method according to [4] above, wherein the ligand is 5-aminolevulinic acid or porphobilinogen.

[5a] The screening method according to [4] above, wherein the ligand is 5-aminolevulinic acid.

[5b] The screening method according to [4] above, wherein the ligand is porphobilinogen.

[6] A kit for screening a compound or its salt that alters the binding property of a G protein-coupled receptor protein comprising the same or substantially the same amino acid sequence as the amino acid sequence represented by SEQ ID NO: 1, or a salt thereof, to a ligand or a salt thereof, which comprises (1) said receptor protein, a partial peptide thereof, or a salt thereof and (2) said ligand or a salt thereof.

[7] The screening kit according to [6] above, wherein the ligand is 5-aminolevulinic acid or porphobilinogen.

[7a] The screening kit according to [6] above, wherein the ligand is 5-aminolevulinic acid.

[7b] The screening kit according to [6] above, wherein the ligand is porphobilinogen.

[8] A kit for screening an agonist or antagonist of a G protein-coupled receptor protein comprising the same or substantially the same amino acid sequence as the amino acid sequence represented by SEQ ID NO: 1, or a salt thereof, which comprises (1) said receptor protein, a partial peptide thereof, or a salt thereof and (2) a compound or its salt that alters the binding property of said ligand or a salt thereof to said receptor protein or a salt thereof.

[9] The screening kit according to [8] above, wherein the ligand is 5-aminolevulinic acid or porphobilinogen.

[9a] The screening kit according to [8] above, wherein the ligand is 5-aminolevulinic acid.

[9b] The screening kit according to [8] above, wherein the ligand is porphobilinogen.

[10] A pharmaceutical which comprises a compound or its salt that alters the binding property of a ligand or a salt thereof to a G protein-coupled receptor protein comprising the same or substantially the same amino acid sequence as the amino acid sequence represented by SEQ ID NO: 1, or a salt thereof.

[11] A preventive/therapeutic agent for nervous system disease or neuropathic pain, which comprises a ligand for a G protein-coupled receptor protein comprising the same or substantially the same amino acid sequence as the amino acid sequence represented by SEQ ID NO: 1, or a salt thereof.

[12] A preventive/therapeutic agent for nervous system disease or neuropathic pain, which comprises an agonist of a G protein-coupled receptor protein comprising the same or substantially the same amino acid sequence as the amino acid sequence represented by SEQ ID NO: 1, or a salt thereof.

[13] A preventive/therapeutic agent for nervous system disease, which comprises an antagonist of a G protein-coupled receptor protein comprising the same or substantially the same amino acid sequence as the amino acid sequence represented by SEQ ID NO: 1, or a salt thereof.

[14] A method of screening an agonist of a G protein-coupled receptor protein comprising the same or substantially the same amino acid sequence as the amino acid sequence represented by SEQ ID NO: 1, or a salt thereof, which comprises comparing changes in the binding property or signal transduction between the case where a ligand or a salt thereof is brought in contact with a cell containing said receptor protein and the case where a test compound is brought in contact with a cell containing said receptor protein.

[15] A method of screening an antagonist of a G protein-coupled receptor protein comprising the same or substantially the same amino acid sequence as the amino acid sequence represented by SEQ ID NO: 1, or a salt thereof, which comprises determining changes in the binding property or signal transduction when a test compound is brought in contact with a cell containing said receptor protein, in the presence of a ligand or a salt thereof.

[16] A preventive/therapeutic agent for nervous system disease or neuropathic pain, which comprises a G protein-coupled receptor protein comprising the same or substantially the same amino acid sequence as the amino acid sequence represented by SEQ ID NO: 1, a partial peptide thereof, or a salt thereof.

[17] A preventive/therapeutic agent for nervous system disease or neuropathic pain, which comprises a polynucleotide comprising a polynucleotide encoding a G protein-coupled receptor protein comprising the same or substantially the same amino acid sequence as the amino acid sequence represented by SEQ ID NO: 1, or a partial peptide thereof.

[18] A diagnostic agent for nervous system disease or neuropathic pain, which comprises a polynucleotide comprising a polynucleotide encoding a G protein-coupled receptor protein comprising the same or substantially the same amino acid sequence as the amino acid sequence represented by SEQ ID NO: 1, or a partial peptide thereof.

[19] A preventive/therapeutic agent for nervous system disease, which comprises an antibody to a G protein-coupled receptor protein comprising the same or substantially the same amino acid sequence as the amino acid sequence represented by SEQ ID NO: 1, a partial peptide thereof, or a salt thereof.

[20] A diagnostic agent for nervous system disease or neuropathic pain, which comprises an antibody to a G protein-coupled receptor protein comprising the same or substantially the same amino acid sequence as the amino acid sequence represented by SEQ ID NO: 1, a partial peptide thereof, or a salt thereof.

[21] A preventive/therapeutic agent for nervous system disease, which comprises a polynucleotide comprising an entire or part of the base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof.

[22] A method of preventing/treating nervous system disease or neuropathic pain, which comprises administering to a mammal an effective amount of (i) a G protein-coupled receptor protein comprising the same or substantially the same amino acid sequence as the amino acid sequence represented by SEQ ID NO: 1, a partial peptide thereof, or a salt thereof, (ii) a polynucleotide comprising a polynucleotide encoding said receptor protein or a partial peptide thereof, (iii) an agonist of said receptor protein or a salt thereof, or (iv) a ligand of said receptor protein or a salt thereof.

[23] A method of preventing/treating nervous system disease, which comprises administering to a mammal an effective amount of (i) an antibody to a G protein-coupled receptor protein comprising the same or substantially the same amino acid sequence as the amino acid sequence represented by SEQ ID NO: 1, a partial peptide thereof, or a salt thereof, (ii) a polynucleotide comprising an entire or part of the base sequence complementary to a polynucleotide comprising a polynucleotide encoding said receptor protein or a partial peptide thereof, or (iii) an antagonist of said receptor protein or a salt thereof.

[24] Use of (i) a G protein-coupled receptor protein comprising the same or substantially the same amino acid sequence as the amino acid sequence represented by SEQ ID NO: 1, a partial peptide thereof, or a salt thereof, (ii) a polynucleotide comprising a polynucleotide encoding said receptor protein or a partial peptide thereof, (iii) an agonist of said receptor protein or a salt thereof, or (iv) a ligand of said receptor protein or a salt thereof, to produce a preventive/therapeutic agent for nervous system disease or neuropathic pain.

[24a] Use of a G protein-coupled receptor protein comprising the same or substantially the same amino acid sequence as the amino acid sequence represented by SEQ ID NO: 1, a partial peptide thereof, or a salt thereof, to produce a preventive/therapeutic agent for nervous system disease or neuropathic pain.

[24b] Use of a polynucleotide comprising a polynucleotide encoding said receptor protein or a partial peptide thereof, to produce a preventive/therapeutic agent for nervous system disease or neuropathic pain.

[24c] Use of an agonist of said receptor protein or a salt thereof to produce a preventive/therapeutic agent for nervous system disease or neuropathic pain.

[24d] Use of a ligand of said receptor protein or a salt thereof, to produce a preventive/therapeutic agent for nervous system disease or neuropathic pain.

[25] Use of (i) an antibody to a G protein-coupled receptor protein comprising the same or substantially the same amino acid sequence as the amino acid sequence represented by SEQ ID NO: 1, a partial peptide thereof, or a salt thereof, (ii) a polynucleotide comprising an entire or part of the base sequence complementary to a polynucleotide comprising a polynucleotide encoding said receptor protein or a partial peptide thereof, or (iii) an antagonist of said receptor protein or a salt thereof, to produce a preventive/therapeutic agent for nervous system disease.

[25a] Use of an antibody to a G protein-coupled receptor protein comprising the same or substantially the same amino acid sequence as the amino acid sequence represented by SEQ ID NO: 1, a partial peptide thereof, or a salt thereof, to produce a preventive/therapeutic agent for nervous system disease.

[25b] Use of a polynucleotide comprising an entire or part of the base sequence complementary to a polynucleotide comprising a polynucleotide encoding said receptor protein or a partial peptide thereof, to produce a preventive/therapeutic agent for nervous system disease.

[25c] Use of an antagonist of said receptor protein or a salt thereof, to produce a preventive/therapeutic agent for nervous system disease.

[26] A method of preventing/treating nervous system disease or neuropathic pain, which comprises promoting the activity of a G protein-coupled receptor protein comprising the same or substantially the same amino acid sequence as the amino acid sequence represented by SEQ ID NO: 1, a partial peptide thereof, or a salt thereof, or the activity of a ligand to said receptor protein.

[27] A method of preventing/treating nervous system disease, which comprises inhibiting the activity of a G protein-coupled receptor protein comprising the same or substantially the same amino acid sequence as the amino acid sequence represented by SEQ ID NO: 1, a partial peptide thereof, or a salt thereof, or the activity of a ligand to said receptor protein.

Hereinafter, the "protein comprising the same or substantially the same amino acid sequence as the amino acid sequence represented by SEQ ID NO: 1, a partial peptide thereof, or a salt thereof" is sometimes briefly referred to as "the receptor of the present invention" or "the protein of the present invention."

The present invention further provides:

(i) a method of screening a compound that alters the binding properties of the ligand of the present invention to the receptor of the present invention, which comprises determining the GTPγS binding-promoting activities on a cell membrane fraction of the receptor of the present invention in the case where the ligand of the present invention is brought in contact with the cell membrane fraction of the receptor of the present invention in the presence of labeled GTPγS and in the case where the ligand of the present invention and a test compound are brought in contact with the cell membrane fraction of the receptor of the present invention in the presence of labeled GTPγS, and comparing the activities;

(ii) a method of screening a compound that alters the binding properties of the ligand of the present invention to the receptor of the present invention, which comprises determining the intracellular cAMP levels in the cell as defined below, between the case where the ligand of the present invention is brought in contact with the cell wherein the receptor of the present invention is expressed, and the case where the ligand of the present invention and a test compound are brought in contact with the cell wherein the receptor of the present invention is expressed, and comparing the cAMP levels;

(iii) a method of screening a compound that alters the binding properties of the ligand of the present invention to the receptor of the present invention, which comprises determining the enzyme activities of a reporter gene protein in the case where the ligand of the present invention is brought in contact with a cell transfected with a CRE-reporter gene vector wherein the receptor of the present invention is expressed and in the case where the ligand of the present invention and a test compound are brought in contact with the cell transfected with a CRE-reporter gene vector wherein the receptor of the present invention is expressed, and comparing the activities;

(iv) a method of screening a compound that alters the binding properties of the ligand of the present invention to the receptor of the present invention, which comprises determining the enzyme activities in the case where the ligand of the present invention is brought in contact with a cell transfected with a SRE-reporter gene vector wherein the receptor of the present invention is expressed and in the case where the ligand of the present invention and a test compound are brought in contact with the cell transfected with a SRE-reporter gene vector wherein the receptor of the present invention is expressed, and comparing the activities;

(v) a method of screening a compound that alters the binding properties of the ligand of the present invention to the receptor of the present invention, which comprises determining the arachidonic acid metabolite-releasing activities in the case where the ligand of the present invention is brought in contact with a cell containing labeled arachidonic acid wherein the receptor of the present invention is expressed and in the case where the ligand of the present invention and a test compound are brought in contact with the cell containing labeled arachidonic acid wherein the receptor of the present invention is expressed, and comparing the activities;

(vi) a method of screening a compound that alters the binding properties of the ligand of the present invention to the receptor of the present invention, which comprises determining the intracellular calcium level increasing activities in the case where the ligand of the present invention is brought in contact with a cell wherein the receptor of the present invention is expressed and in the case where the ligand of the present invention and a test compound are brought in contact with the cell wherein the receptor of the present invention is expressed, and comparing the activities;

(vii) a method of screening a compound that alters the binding properties of the ligand of the present invention to the receptor of the present invention, which comprises determining the inositol triphosphate producing activities in the presence of labeled inositol, in the case where the ligand of the present invention is brought in contact with the cell wherein the receptor of the present invention is expressed and in the case where the ligand of the present invention and a test compound are brought in contact with the cell wherein the receptor of the present invention is expressed, and comparing the activities;

(viii) a method of screening a compound that alters the binding properties of the ligand of the present invention to the receptor of the present invention, which comprises determining the enzyme activities in the case where the ligand of the present invention is brought in contact with the cell transfected with a TRE-reporter gene vector wherein the receptor of the present invention is expressed and in the case where the ligand of the present invention and a test compound are brought in contact with the cell transfected with a TRE-reporter gene vector wherein the receptor of the present invention is expressed, and comparing the activities;

(ix) a method of screening a compound that alters the binding properties of the ligand of the present invention to the receptor of the present invention, which comprises determining the cell growth in the case where the ligand of the present invention is brought in contact with a cell wherein the receptor of the present invention is expressed and in the case where the ligand of the present invention and a test compound are brought in contact with the cell wherein the receptor of the present invention is expressed, and comparing the cell growth;

(x) a method of screening a compound that alters the binding properties of the ligand of the present invention to the receptor of the present invention, which comprises determining the efflux activities of labeled rubidium in the case where the ligand of the present invention is brought in contact with the cell in the presence of labeled rubidium wherein the receptor of the present invention is expressed and in the case where the ligand of the present invention and a test compound are brought in contact with the cell in the presence of labeled rubidium wherein the receptor of the present invention is expressed, and comparing the activities;

(xi) a method of screening a compound that alters the binding properties of the ligand of the present invention to the receptor of the present invention, which comprises determining the extracellular pH changes in the case where the ligand of the present invention is brought in contact with the cell wherein the receptor of the present invention is expressed and in the case where the ligand of the present invention and a test compound are brought in contact with the cell wherein the receptor of the present invention is expressed, and comparing the changes;

(xii) a method of screening a compound that alters the binding properties of the ligand of the present invention to the receptor of the present invention, which comprises culturing, in a histidine-deficient medium, a yeast transfected with a histidine synthetic gene wherein the receptor of the present invention is expressed, contacting with the ligand of the present invention or with the ligand of the present invention and a test compound, determining the growth of the yeast, and comparing the growth;

(xiii) a method of screening a compound that alters the binding properties of the ligand of the present invention to the receptor of the present invention, which comprises determining the changes in cell membrane potential in the case where the ligand of the present invention is brought in contact with the *Xenopus laevis* oocytes where RNA of a gene for the receptor of the present invention is transfected and in the case where the ligand of the present invention and a test compound are brought in contact with the *Xenopus laevis* oocytes where RNA of a gene for the receptor of the present invention is transfected, and comparing the changes; and so on.

BEST MODE FOR CARRYING OUT THE INVENTION

Figure 1:
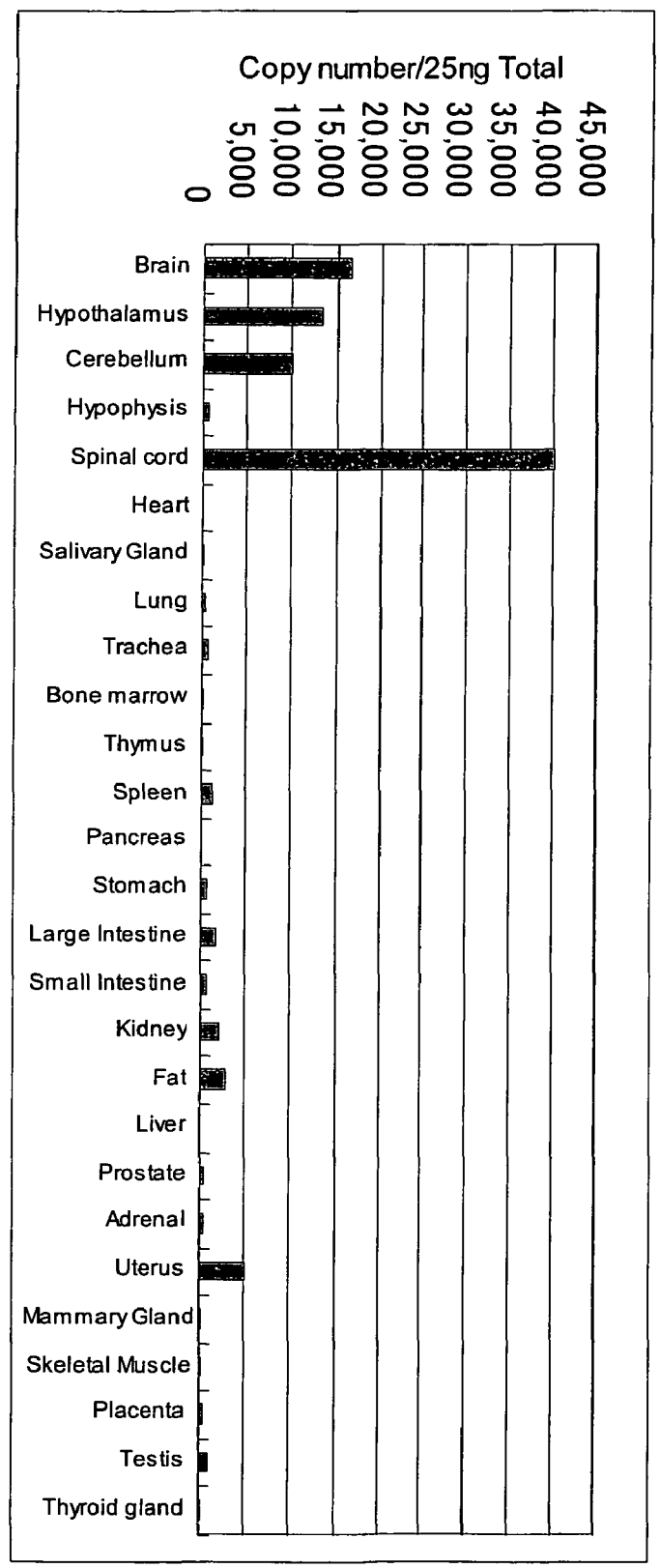
FIG. 1 shows the expression distribution of GPR17 mRNA in various human tissues.

The receptor proteins comprising the same or substantially the same amino acid sequences as the amino acid sequences represented by SEQ ID NO: 1 are sometimes briefly referred to as the "GPR17" in the specification.

The GPR17 may be any protein derived from any cell (e.g., splenocyte, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.) or hematocyte type cells; or any tissues where such cells are present, such as brain or any of brain regions (e.g., olfactory bulb, amygdaloid nucleus, basal ganglia, hippocampus, thalamus, hypothalamus, subthalamic nucleus, cerebral cortex, medulla oblongata, cerebellum, occipital lobe, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, digestive tract (e.g., large intestine and small intestine), intestinal tract, blood vessel, heart, thymus, spleen, submandibular gland, peripheral blood, peripheral blood cell, prostate, testis, ovary, placenta, uterus, bone, joint, skeletal muscle, etc. of human and mammals (e.g., guinea pig, rat, mouse, rabbit, swine, sheep, bovine, monkey, etc.), in particular, any protein derived from immunocompetent organs and immunocompetent cells such as spleen, bone marrow, intestinal tract, monocytes, macrophages, etc.; the proteins may also be synthetic proteins.

The amino acid sequence which has substantially the same amino acid sequence as that represented by SEQ ID NO: 1 includes an amino acid sequence having at least about 85% homology, preferably at least about 90% homology and more preferably at least about 95% homology, to the amino acid sequence represented by SEQ ID NO: 1; etc. Homology of the amino acid sequences can be measured under the following conditions (an expectation value=10; gaps are allowed; matrix=BLOSUM62; filtering=OFF) using a homology scoring algorithm NCBI BLAST (National Center for Biotechnology Information Basic Local Alignment Search Tool).

Preferably, the protein comprising substantially the same amino acid sequence as the amino acid sequence represented by SEQ ID NO: 1 is, for example, a protein comprising substantially the same amino acid sequence as the amino acid sequence represented by SEQ ID NO: 1 and having the activity substantially equivalent to that of the GPR17 comprising the amino acid sequence represented by SEQ ID NO: 1, or the like.

As the substantially equivalent activity, there is, for example, a ligand binding activity, signal transduction action, or the like. The substantially equivalent is used to mean that the nature of the activity is equivalent in terms of quality. Thus, the activity such as the ligand binding activity, signal transduction action or the like is preferably equivalent (e.g., about 0.01 to 100 times, preferably about 0.5 to 20 times, more preferably 0.5 to 2 times), but differences in quantitative factors such as a level of these activities, a molecular weight of the protein, etc. may be present and allowable. The activities such as ligand binding activities, signal transduction actions or the like can be determined according to publicly known methods with some modifications thereof, for example, it can be determined by the screening methods that will be later described.

Also, proteins comprising the following amino acid sequences are used as the GPR17: a) amino acid sequences wherein at least 1 or 2 amino acids (preferably approximately 1 to 30 amino acids, more preferably approximately 1 to 10 amino acids, most preferably several (1 to 5) amino acids) are deleted of the amino acid sequence represented by SEQ ID NO: 1; b) amino acid sequences wherein at least 1 or 2 amino acids (preferably approximately 1 to 30 amino acids, more preferably approximately 1 to 10 amino acids, and most preferably several (1 to 5) amino acids) are added to the amino acid sequence represented by SEQ ID NO: 1; c) amino acid sequences wherein at least 1 or 2 amino acids (preferably approximately 1 to 30 amino acids, more preferably approximately 1 to 10 amino acids, and most preferably several (1 to 5) amino acids) in the amino acid sequence represented by SEQ ID NO: 1 are substituted by other amino acids; or d) amino acid sequences which are combination of these; and the like.

Throughout the present specification, the protein is represented in accordance with the conventional way of describing peptides, that is, the N-terminus (amino terminus) at the left hand and the C-terminus (carboxyl terminus) at the right hand. In the GPR17 including the GPR17 comprising the amino acid sequence represented by SEQ ID NO: 1, the C-terminus may be in any form of a carboxyl group (—COOH), carboxylate (—COO⁻), an amide (—CONH$_2$) or an ester (—COOR).

Examples of R in the ester include a $C_{1-6}$ alkyl group such as methyl, ethyl, n-propyl, isopropyl or n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

Where the GPR17 contains a carboxyl group (or a carboxylate) at a position other than the C-terminus, it may be amidated or esterified and such an amide or ester is also included within the GPR17 of the present invention. The ester group may be the same group as that described with respect to the C-terminus described above.

Furthermore, examples of the GPR17 include variants of the above proteins, wherein the amino group at the N-terminal methionine residue of the protein supra is protected with a protecting group (for example, a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as so-called glycoproteins having sugar chains bound thereto.

As a specific example of the GPR17 of the present invention, there is employed, for example, human-derived GPR17 (J. Leukoc. Biol., 59 (1), 18-23 (1996), WO9412635) consisting of the amino acid sequence represented by SEQ ID NO: 1.

As a partial peptide of the GPR17 (hereinafter sometimes referred to as the partial peptide), any partial peptide can be used so long as it is a peptide having a part of the amino acid sequence of the GPR17 described above. For example, among protein molecules of the GPR17, those having a site exposed to the outside of a cell membrane and having substantially the same receptor binding activity can be used.

Specifically, the partial peptide of the GPR17 having the amino acid sequence represented by SEQ ID NO: 1 is a peptide containing the parts analyzed to be extracellular domains (hydrophilic domains) in the hydrophobic plotting analysis. A peptide containing the hydrophobic domain in part can be used as well. In addition, the peptide may contain each domain separately or plural domains together.

In the partial peptides of the present invention, preferred are peptides having at least 20, preferably at least 50, and more preferably at least 100 amino acids, in the amino acid sequence which constitutes the receptor protein of the present invention described above.

The amino acid sequence having substantially the same amino acid sequence includes an amino acid sequence having at least about 85% homology, preferably at least about 90% homology and more preferably at least about 95% homology, to these amino acid sequences. Homology of the amino acid sequences can be measured under the same conditions using the same homology scoring algorithm NCBI BLAST as described above.

Herein the term "substantially the same receptor activity" has the same significance as described above. The "substantially the same receptor activity" can be assayed by the same manner as described above.

In the amino acid sequence described above, the partial peptide of the present invention may contain amino acid sequences, of which at least 1 or 2 amino acids (preferably approximately 1 to 10 amino acids, more preferably several (1 to 5) amino acids) are deleted; to which at least 1 or 2 amino acids (preferably approximately 1 to 20 amino acids, more preferably approximately 1 to 10 amino acids, and most preferably several (1 to 5) amino acids) are added; or, in which at least 1 or 2 amino acids (preferably approximately 1 to 10 amino acids, more preferably several and most preferably approximately 1 to 5 amino acids) are substituted by other amino acids.

In the partial peptide of the present invention, the C-terminus may be in any form of a carboxyl group (—COOH), carboxylate (—COO$^-$), an amide (—CONH$_2$) or an ester (—COOR). Where the partial peptide of the present invention contains a carboxyl group (or a carboxylate) at a position other than the C-terminus, it may be amidated or esterified and such an amide or ester is also included within the partial peptide of the present invention. In this case, the ester group may be the same group as that described with respect to the C-terminus described above.

As in the GPR17 described above, the partial peptide of the present invention further includes those in which the amino group of the amino acid residue of the N-terminal methionine residue is protected by a protecting group, those in which the N-terminal residue is cleaved in vivo and the produced glutamine residue is pyroglutaminated, those in which substituents on the side chains of amino acids in the molecule are protected by appropriate protecting groups, conjugated peptides such as so-called glycopeptides, to which sugar chains are bound, and the like.

For salts of the GPR17 of the present invention or its partial peptide, preferred are physiologically acceptable salts with acids or bases, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The GPR17 of the present invention or its salts can be manufactured from the human or mammalian cells or tissues described above by publicly known methods for purification of receptor proteins, or by culturing transformants bearing DNA encoding the GPR17 of the present invention later described. Alternatively, the GPR17 or its salts can also be manufactured by protein synthesis method or its modifications later described. Where they are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the GPR17 of the present invention or its partial peptides, or salts or amides thereof, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective protein according to various condensation methods publicly known in the art. At the end of the reaction, the protein is cut out from the resin and at the same time, the protecting groups are removed. Then, intramolecular disulfide bond-forming reaction is performed in a highly diluted solution to obtain the objective protein or its amides.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitrites such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20 to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, tertiary pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, tertiary butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester), phenacyl esterification, benzyloxycarbonyl hydrazidation, tertiary butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br—Z, tertiary butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups used in the starting compounds include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)), etc.

As the activated amino acids, in which the amino groups are activated in the starting material, for example, the corresponding phosphoric amides are employed.

To eliminate (split off) the protecting groups, there are used catalytic reduction under hydrogen gas flow in the presence of a catalyst such as Pd-black, Pd-carbon, etc.; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia. The elimination of the protecting group by the acid treatment described above is carried out generally at a temperature of approximately −20 to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups, activation of functional groups involved in the reaction, or the like may be appropriately selected from publicly known groups and publicly known means.

In another method for obtaining the amides of the protein, for example, the α-carboxyl group of the carboxy terminal amino acid is first protected by amidation; the peptide (protein) chain is then extended from the amino group side to a desired length. Thereafter, a protein in which only the protecting group of the N-terminal α-amino group in the peptide chain has been eliminated from the protein and a protein in which only the protecting group of the C-terminal carboxyl group has been eliminated are prepared. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. Lyophilization of the major fraction gives the amide of the desired protein.

To prepare the esterified protein, for example, the α-carboxyl group of the carboxy terminal amino acid is condensed with a desired alcohol to prepare the amino acid ester, which is followed by procedure similar to the preparation of the amidated protein above to give the ester form of the desired protein.

The partial peptide or its salts of the GPR17 of the present invention can be manufactured by publicly known methods for peptide synthesis, or by cleaving the GPR17 of the present invention with an appropriate peptidase. For the methods for peptide synthesis, for example, either solid phase synthesis or liquid phase synthesis may be used. That is, the partial peptide or amino acids that can construct the GPR17 of the present invention are condensed with the remaining part. Where the product contains protecting groups, these protecting groups are removed to give the desired peptide. Publicly known methods for condensation and elimination of the protecting groups are described in a)-e) below.

a) M. Bodanszky & M. A. Ondetti: Peptide Synthesis, Interscience Publishers, New York (1966)

b) Schroeder & Luebke: The Peptide, Academic Press, New York (1965)

c) Nobuo Izumiya, et al.: *Peptide Gosei-no-Kiso to Jikken* (Basics and experiments of peptide synthesis), published by Maruzen Co. (1975)

d) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

e) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the methods above is in a free form, the peptide can be converted into an appropriate salt by a publicly known method; conversely when the peptide is obtained in a salt form, it can be converted into a free form by a publicly known method.

The polynucleotide encoding the GPR17 of the present invention may be any polynucleotide so long as it contains the base sequence (DNA or RNA, preferably DNA) encoding the GPR17 of the present invention described above. Such a polynucleotide may also be any one of DNA encoding the GPR17 of the present invention, or RNA such as mRNA, etc., and may be double-stranded or single-stranded. Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a non-coding strand).

Using the polynucleotide encoding the GPR17 of the present invention, mRNA of the GPR17 of the present invention can be quantified by, for example, the publicly known method published in separate volume of *Jikken Igaku* 15 (7) "New PCR and its application" (1997), or by its modifications.

The DNA encoding the GPR17 of the present invention may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding the human GPR17 of the present invention may be any DNA, so long as it is, for example, a DNA containing the base sequence represented by SEQ ID NO: 2, or any DNA having a base sequence hybridizable to the base sequence represented by SEQ ID NO: 2 under high stringent conditions and encoding a receptor protein which has the activities substantially equivalent to those of human GPR17 consisting of the amino acid sequence represented by SEQ ID NO: 1 (e.g., the ligand-binding activity, the signal transduction action, etc.).

Examples of the DNA hybridizable to the DNA containing the base sequence represented by SEQ ID NO: 2 include a DNA containing a base sequence having at least about 85% homology, preferably at least about 90% homology and more preferably at least about 95% homology, to the base sequence represented by SEQ ID NO: 2. Homology of the base sequences can be measured under the following conditions (an expectation value=10; gaps are allowed; filtering=ON, match score=1, mismatch score=−3) using a homology scoring algorithm NCBI BLAST (National Center for Biotechnology Information Basic Local Alignment Search Tool).

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions. The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, as a DNA encoding the human GPR17 consisting of the amino acid sequence represented by SEQ ID NO: 1, there may be employed a DNA consisting of the base sequence represented by SEQ ID NO: 2; etc.

The polynucleotide comprising a part of the base sequence of the DNA encoding the GPR17 of the present invention or a part of the base sequence complementary to the DNA is used to mean that the polynucleotide embraces not only the DNA encoding the partial peptide of the present invention described below but also RNA.

According to the present invention, antisense polynucleotides (nucleic acids) that can inhibit the replication or expression of the GPR17 genes can be designed and synthesized based on the base sequence information of the cloned or determined DNA encoding the GPR17. Such a polynucleotide (nucleic acid) is capable of hybridizing to RNA of the GPR17 gene to inhibit the synthesis or function of said RNA or capable of modulating or controlling the expression of the GPR17 gene via interaction with the GPR17-associated RNA. Polynucleotides complementary to the selected sequences of the GPR17-associated RNA and polynucleotides specifically hybridizable to the GPR17-associated RNA are useful in modulating or controlling the expression of the GPR17 gene in vivo and in vitro, and useful for the treatment or diagnosis of diseases. The term "corresponding" is used to mean homologous to or complementary to a particular sequence of the nucleotide, base sequence or nucleic acid including the gene. The term "corresponding" between nucleotides, base sequences or nucleic acids and peptides (proteins) usually refer to amino acids of a peptide (protein) under the order derived from the sequence of nucleotides (nucleic acids) or their complements. In the GPR17 gene, the 5' end hairpin loop, 5' end 6-base-pair repeats, 5' end untranslated region, polypeptide translation initiation codon, protein coding region, translation termination codon, 3' end untranslated region, 3' end palindrome region, and 3' end hairpin loop, may be selected as preferred target regions, though any other region may be selected as a target in the GPR17 gene.

The relationship between the targeted nucleic acids and the hybridizable polynucleotides complementary to at least a part of the target can be denoted to be "antisense" to the target. Examples of the antisense polynucleotides include polydeoxyribonucleotide containing 2-deoxy-D-ribose, polyribonucleotide containing D-ribose, any other type of polynucleotides which are N-glycosides of a purine or pyrimidine base, or other polymers containing non-nucleotide backbones (e.g., protein nucleic acids and synthetic sequence-specific nucleic acid polymers commercially available) or other polymers containing nonstandard linkages (provided that the polymers contain nucleotides having such a configuration that allows base pairing or base stacking, as is found in DNA or RNA), etc. They may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acid of the present invention may contain changed or modified sugars, bases or linkages. The antisense nucleic acid may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or the translation system of the G protein-coupled receptor protein in vivo and in vitro. The nucleic acid can be applied to cells by a variety of publicly known methods.

The DNA encoding the partial peptide of the present invention may be any DNA so long as it contains the base sequence encoding the partial peptide of the present invention described above. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using mRNA fraction prepared from the cells and tissues described above.

Specifically, the DNA encoding the partial peptide of the present invention may be any one of, for example, (1) a DNA containing a partial base sequence of the DNA having the base sequence represented by SEQ ID NO: 2, or (2) any DNA containing a partial base sequence of the DNA having a DNA hybridizable to the DNA represented by SEQ ID NO: 2 under highly stringent conditions and encoding the receptor protein which has the activities (e.g., the ligand-biding activity, the signal transduction action, etc.) substantially equivalent to those of the GPR17 consisting of the amino acid sequences represented by SEQ ID NO: 1; etc.

Examples of the DNA that is hybridizable to the base sequence represented by SEQ ID NO: 2 include DNA containing a base sequence having at least about 85% homology, preferably at least about 90% homology and more preferably at least about 95% homology, to the base sequence represented by SEQ ID NO: 2.

Homology of the base sequences can be measured under the same conditions using the homology scoring algorithm NCBI BLAST described above.

The method and conditions of hybridization are the same as described above.

For cloning of the DNA that completely encodes the GPR17 of the present invention or its partial peptide (hereinafter sometimes collectively referred to as the GPR17 of the present invention), the DNA may be amplified by PCR using synthetic DNA primers containing a part of the base sequence of the GPR17 of the present invention, or the DNA inserted into an appropriate vector can be selected by hybridization with a labeled DNA fragment or synthetic DNA that encodes a part or entire region of the GPR17 of the present invention. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Substitution of the base sequence of the DNA can be effected by publicly known methods such as the ODA-LA PCR method, the Gapped duplex method or the Kunkel method or its modifications by PCR or using publicly known kits available as Mutan™-superExpress Km (manufactured by TaKaRa Shuzo Co., Ltd.), Mutan™-K (manufactured by TaKaRa Shuzo Co., Ltd.), etc.

The cloned DNA encoding the GPR17 can be used as it is, depending upon purpose or, if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof. These translation initiation and termination codons may also be added by using an appropriate synthetic DNA adapter.

The expression vector for the GPR17 of the present invention can be manufactured, for example, by (a) excising the desired DNA fragment from the DNA encoding the GPR17 of the present invention, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc. Among them, CMV promoter or SRα promoter is preferably used. Where the host is bacteria of the genus *Escherichia*, preferred examples of the promoter include trp promoter, lac promoter, recA promoter, $\lambda P_L$ promoter, lpp promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a polyA addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is used as the selection marker in CHO (dhfr$^-$) cells, selection can also be made on thymidine free media.

If necessary, a signal sequence that matches with a host is added to the N-terminus of the receptor protein of the present invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector bearing the DNA encoding the GPR17 of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)), JM103 (Nucleic Acids Research, 9, 309 (1981)], JA221 [Journal of Molecular Biology, 120, 517 (1978)], HB101 [Journal of Molecular Biology, 41, 459 (1969)), C600 (Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R$^-$, NA87-11A, DKD-5D, 20B-12, *Schizosaccharomyces pombe* NCYC1913, NCYC2036, *Pichia pastoris*, etc.

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. are used. Examples of the Sf cell which can be used are Sf9 cells (ATCC CRL1711) and Sf21 cells (both cells are described in Vaughn, J. L. et al., In Vivo, 13, 213-217 (1977)), etc.

As the insect, for example, a larva of *Bombyx mori*, etc. can be used [Maeda, et al., Nature, 315, 592 (1985)].

Examples of animal cells include monkey cells COS-7, Vero, Chinese hamster cells CHO (hereinafter referred to as CHO cells), dhfr gene deficient Chinese hamster cells CHO (hereinafter briefly referred to as CHO (dhfr$^-$) cell), mouse L cells, mouse AtT-20, mouse myeloma cells, rat GH3, human FL cells, human HeLa cells, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995) (published by Shujunsha), or Virology, 52, 456 (1973).

Thus, the transformant transformed with the expression vector containing the DNA encoding GPR17 can be obtained.

Where the host is bacteria belonging to the genus *Escherichia* or the genus *Bacillus*, the transformant can be appropriately incubated in a liquid medium which contains materials required for growth of the transformant such as carbon sources, nitrogen sources, minerals, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the minerals are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431-433, Cold Spring Harbor Laboratory, New York, 1972). If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultivated generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the GPR17 of the present invention can be produced into the cell, in the cell membrane or out of the cell of the transformant.

The GPR17 of the present invention can be separated and purified from the culture described above by the following procedures.

When the GPR17 of the present invention is extracted from the culture or cells, after cultivation the transformants or cells are collected by a publicly known method and suspended in an appropriate buffer. The transformants or cells are then disrupted by publicly known methods such as ultrasonication, a treatment with lysozyme and/or freeze-thaw cycling, followed by centrifugation, filtration, etc. Thus, the crude extract of the GPR17 can be obtained. The buffer used for the procedures may contain a protein denaturant such as urea or guanidine hydrochloride, or a surfactant such as Triton X-100™, etc. When the GPR17 is secreted in the culture medium, after completion of the cultivation, the supernatant can be separated from the transformants or cells to collect the supernatant by a publicly known method.

The GPR17 contained in the culture supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

In the case where the GPR17 thus obtained is in a free form, it can be converted into the salt by publicly known methods or modifications thereof. On the other hand, when the GPR17 is obtained in the form of a salt, it can be converted into the free form or in the form of a different salt by publicly known methods or modifications thereof.

The GPR17 produced by the recombinant can be treated, prior to or after the purification, with an appropriate protein modifying enzyme to appropriately modify the same or partially remove a polypeptide. Examples of the protein-modifying enzyme include trypsin, chymotrypsin, arginyl endopeptidase, protein kinase, glycosidase, or the like.

The activity of the thus produced the GPR17 of the present invention can be determined by a binding experiment to a labeled ligand (ligand peptide), by an enzyme immunoassay using a specific antibody, or the like.

Antibodies to the GPR17 of the present invention may be any of polyclonal antibodies and monoclonal antibodies, as long as they are capable of recognizing the GPR17 of the present invention.

The antibodies to the GPR17 of the present invention may be manufactured by publicly known methods for manufacturing antibodies or antisera, using as antigens the GPR17 of the present invention.

[Preparation of Monoclonal Antibody]

(a) Preparation of Monoclonal Antibody-Producing Cells

The GPR17 of the present invention is administered to mammals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the applicable mammals are monkeys, rabbits, dogs, guinea pigs, mice, rats, sheep and goats, with mice and rats being preferred.

In the preparation of monoclonal antibody-producing cells, warm-blooded animals, e.g., mice, immunized with an antigen wherein the antibody titer is noted is selected, then the spleen or lymph node is collected after 2 to 5 days from the final immunization and antibody-producing cells contained therein are fused with myeloma cells to give monoclonal antibody-producing hybridomas. Measurement of the antibody titer in antisera may be made, for example, by reacting a labeled form of the receptor protein, which will be described later, with the antiserum followed by assaying the binding activity of the labeling agent bound to the antibody. The fusion may be operated, for example, by the known Koehler and Milstein method [Nature, 256, 495 (1975)]. Examples of the fusion accelerator are polyethylene glycol (PEG), Sendai virus, etc., of which PEG is preferably employed.

Examples of the myeloma cells are NS-1, P3U1, SP2/0, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at about 20 to about 40° C., preferably at about 30 to about 37° C. for about 1 to about 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with an antigen of the receptor protein directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the receptor protein labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at about 37° C., for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc. and dissociating the binding to obtain the antibody].

[Preparation of Polyclonal Antibody]

The polyclonal antibody of the present invention can be manufactured by publicly known methods or modifications thereof. For example, a complex of immunogen (GPR17 antigen) and a carrier protein is prepared, and a mammal is immunized with the complex in a manner similar to the method described above for the manufacture of monoclonal antibodies. The product containing the antibody to the GPR17 of the present invention is collected from the immunized animal followed by separation and purification of the antibody.

In the complex of an immunogen and a carrier protein used to immunize a mammal, the type of carrier protein and the mixing ratio of a carrier to hapten may be any type and in any ratio, as long as the antibody is efficiently produced to the hapten immunized by crosslinking to the carrier. For example, bovine serum albumin, bovine thyroglobulins, keyhole limpet hemocyanin, etc. is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide activated ester, activated ester reagents containing thiol group or dithiopyridyl group, etc. are used for the coupling.

The condensation product is administered to warm-blooded animals either solely or together with carriers or diluents to the site in which the antibody can be produced by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of mammals immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as applied to the separation and purification of monoclonal antibodies described hereinabove.

The ligands, which bind to the GPR17 (hereinafter sometimes referred to as "the ligands of the present invention" or "ligands"), may be any ligands so long as they are capable of specifically binding to the GPR17. Examples include those having a dissociation constant of 10 µM or less, preferably not greater than 2 µM, more preferably not greater than 1 µM, particularly preferably not greater than 200 nM, and most preferably not greater than 100 nM, in binding to the GPR17.

The ligands of the present invention may be peptides, proteins, antibodies, non-peptide compounds, synthetic compounds, fermentation products, cell extract, plant extract, animal tissue extract, plasma, etc., which may be novel or known.

Preferably, 5-aminolevulinic acid, porphobilinogen, etc. are used as the ligands of the present invention.

As the ligands of the present invention, when they are commercially available, these commercially available ligands can be used as they are. Alternatively, the ligands can be produced or extracted in accordance with publicly known methods or their modifications.

The ligands described above may form salts. As salts thereof, salts with physiologically acceptable acids or bases may be employed, preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), and the like.

Where the ligand is a peptide, the peptide may be any polypeptide derived from any cell (e.g., hepatocyte, splenocyte, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells or interstitial cells; or the corresponding precursor cells, stem cells, cancer cells, etc.) of human and other warm-blooded animals (e.g., guinea pig, rat, mouse, fowl, rabbit, swine, sheep, bovine, monkey, etc.); or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, digestive tract (e.g., large intestine and small intestine), blood vessel, heart, thymus, spleen, salivary gland, peripheral blood, prostate, testis, ovary, placenta, uterus, bone, cartilage, joint, skeletal muscle, etc.; the ligand may also be a recombinant polypeptide or a synthetic polypeptide. Hereinafter, the ligand which is a peptide is referred to as a ligand peptide.

The "substantially equivalent" is used to mean that the physiological properties including the ligand activities, for example, the binding activities to the GPR17, intracellular signal transduction activities, anti-inflammatory actions, etc. are substantially equivalent. In the case of ligand peptides, as far as substitution, deletion, addition or insertion of an amino acid(s) does not cause significant changes in physiological or chemical properties of the ligand peptides, ligand peptides that have undergone such substitution, deletion, addition or insertion are substantially equivalent to intact peptides that do not undergo the substitution, deletion, addition or insertion. Substantially the same substituent(s) of an amino acid(s) in the amino acid sequence can be selected from, e.g., other amino acids of the class, to which the amino acid(s) belong.

Examples of non-polar (hydrophobic) amino acids include alanine, leucine, isoleucine, valine, proline, phenylalanine, tryptophan, methionine, and the like. Examples of polar (neutral) amino acids are glycine, serine, threonine, cysteine, tyrosine, asparagine, glutamine, and the like. Examples of positively charged (basic) amino acids are arginine, lysine, histidine, and the like. Examples of negatively charged (acidic) amino acids include aspartic acid, glutamic acid, and the like.

The ligand peptide also includes a peptide in which a substituent(s) on the side chain of constituent amino acids have been protected by appropriate protective groups, a conjugated peptide such as a so-called glycopeptide having sugar chains bound thereto, or the like. Furthermore, the ligand peptide includes those wherein an optional foreign peptide sequence (for example, FLAG His tag, HA tag, HSV tag, etc.) capable of serving as an epitope (antibody recognition site) is added to each N- or C-terminus, etc.

The ligand peptide is represented in accordance with the conventional way of describing peptides, that is, the N-terminus (amino terminus) at the left hand and the C-terminus (carboxyl terminus) at the right hand. In the ligand peptide including the peptide consisting of the amino acid sequence represented by SEQ ID NO: 1, the C-terminus may be in any form of a carboxyl group (—COOH), carboxylate (—COO$^-$), an amide (—CONH$_2$) or an ester (—COOR), preferably an amide. Herein, examples of R in the ester includes a C$_{1-6}$ alkyl group such as methyl, ethyl, n-propyl, isopropyl or n-butyl, etc.; a C$_{3-8}$ cycloalkyl group such as cyclopentyl, cyclohexyl, etc.; a C$_{6-12}$ aryl group such as phenyl, α-naphthyl, etc.; a C$_{7-14}$ aralkyl group such as a phenyl-C$_{1-2}$-alkyl group, e.g., benzyl, phenethyl, etc., or an α-naphthyl-C$_{1-2}$-alkyl group such as, -naphthylmethyl, etc.; and the like. In addition, pivaloyloxymethyl or the like, which is used widely as an ester for oral administration, may also be used. Where the ligand peptide contains a carboxyl group (or a carboxylate) at a position other than the C-terminus, the carboxyl group may be amidated or esterified and such amide or ester is also included within the ligand peptide in the present specification. In this case, the esters given for the C-terminus described above are employed as the ester.

Furthermore, examples of the ligand peptide include variants wherein the amino group at the N-terminal amino acid residues (e.g., methionine residue) is protected with a protecting group (e.g., a C$_{1-6}$ acyl group such as a C$_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a C$_{1-6}$ acyl group such as a C$_{1-6}$ alkanoyl group, e.g., formyl group, acetyl group, etc.), or conjugated polypeptides such as so-called glycopolypeptides having sugar chains bound thereto; those with modified C-terminal amino acid residues; etc. In particular, peptides wherein the amino group of the N-terminal methionine residue is protected with a formyl group are preferred; in this case, the peptides may further be protected or modified as described above.

The ligand peptide may form salts. As salts thereof, salts with physiologically acceptable acids (e.g., inorganic acids or organic acids) or bases (e.g., alkali metal salts) may be employed, preferably in the form of physiologically acceptable acid addition salts. Examples of such salts include salts with inorganic acids (e.g., hydrochloric acid, phosphoric acid, hydrobromic acid, and sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, and benzenesulfonic acid), etc.

The ligand peptide can be manufactured from the human or non-human warm-blooded animal cells or tissues described above by publicly known methods for purification of polypeptides, or by modifications of peptide synthesis later described. Where they are manufactured from human or non-human mammalian tissues or cells, human or non-human mammalian tissues or cells are homogenized, then extracted with an acid or the like, and the extract is isolated and purified by a combination of chromatography techniques such as reverse phase chromatography, ion exchange chromatography, and the like.

To synthesize the ligand peptide or its amides, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is cut out from the resin and at the same time, the protecting groups are removed. Then, intramolecular disulfide bond-forming reaction is performed in a highly diluted solution to obtain the objective polypeptide or its amides.

For condensation of the protected amino acids described above, a variety of activation reagents for polypeptide synthesis may be used, and carbodiimides are particularly employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of corresponding acid anhydrides, HOBt esters or HOOBt esters, followed by adding the thus activated protected amino acids to the resin.

Solvents suitable for use to activate the protected amino acids or condense with the resin may be chosen from solvents that are known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (linear, branched or cyclic alkyl esterification of, e.g., methyl, ethyl, propyl, butyl, t-butyl, cyclopentyl, cyclohexyl, cycloheptyl, cyclooctyl, 2-adamantyl, etc.), aralkyl esterification (e.g., benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $C_{1-2}$—Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)].

As the amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, or a mixture solution of these acids; a treatment with a base such as diisopropylethylamine, triethylamine, piperidine or piperazine; reduction with sodium in liquid ammonia, etc. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the ligand peptide, for example, the α-carboxyl group of the carboxy terminal amino acid is first protected by amidation; the peptide (polypeptide) chain is then extended from the amino group side to a desired length. Thereafter, a polypeptide, in which only the protecting group of the N-terminal α-amino group of the peptide chain has been eliminated, and a polypeptide, in which only the protecting group of the C-terminal carboxyl group has been eliminated are manufactured. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired ligand peptide.

To prepare the esterified ligand peptide, for example, the α-carboxyl group of the carboxy terminal amino acid is condensed with a desired alcohol to prepare the amino acid ester, which is followed by procedures similar to the preparation of the amidated ligand peptide above to give the desired esterified polypeptide.

The ligand peptide can be manufactured by publicly known methods for peptide synthesis. As the methods for peptide synthesis, for example, either solid phase synthesis or liquid phase synthesis may be used. That is, the partial peptide or amino acids that can constitute the ligand peptide are condensed with the remaining part. Where the product contains protecting groups, these protecting groups are removed to give the desired peptide. Publicly known methods for condensation and elimination of the protecting groups are described in (i) to (v) below.

(i) M. Bodanszky & M. A. Ondetti: Peptide Synthesis, Interscience Publishers, New York (1966)

(ii) Schroeder & Luebke: The Peptide, Academic Press, New York (1965)

(ii) Nobuo Izumiya, et al.: Peptide Gosei-no-Kiso to Jikken (Basics and experiments of peptide synthesis), published by Maruzen Co. (1975)

(iv) Haruaki Yajima & Shunpei Sakakibara: Seikagaku Jikken Koza (Biochemical Experiment) 1, Tanpakushitsu no Kagaku (Chemistry of Proteins) IV, 205 (1977)

(v) Haruaki Yajima ed.: Zoku Iyakuhin no Kaihatsu (A sequel to Development of Pharmaceuticals), Vol. 14, Peptide Synthesis, published by Hirokawa Shoten After completion of the reaction, the polypeptide of the present invention or the partial peptide of the present invention may be purified and isolated by a combination of conventional purification methods such as solvent extraction, distillation, column chromatography, liquid chromatography and recrystallization. When the polypeptide obtained by the above methods is in a free form, it can be converted into an appropriate salt by a publicly known method or its modifications; when the polypeptide is obtained in a salt form, it can be converted into a free form or other different salt form by a publicly known method or its modifications.

The antibody to the ligand peptide can be manufactured in a similar manner to the antibody to the GPR17 of the present invention.

Hereinafter, the ligand, the GPR17, the DNA encoding the GPR17 (hereinafter sometimes referred to as the DNA of the present invention), the antibody to the ligand peptide or the GPR17 (hereinafter sometimes referred to as the antibody of the present invention), and the antisense DNA to the DNA of the present invention (hereinafter referred to as the antisense DNA of the present invention) are described in terms of their use.

(1) Preventive/Therapeutic Agent for Diseases Associated with Dysfunction of the GPR17 of the Present Invention Where the ligand or the GPR17 or polynucleotide (e.g., DNA, etc.) encoding the same involves any abnormality or deficiency, or where its expression is abnormally reduced, various diseases are developed; examples of such diseases are neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

Therefore, when the physiological activities of the ligand cannot be expected in a patient (deficiency of the ligand or the GPR17) due to a decrease of the ligand or the GPR17 in the body, the amount of the ligand or the GPR17 can be increased in the boy of the patient a) by administering the ligand or the GPR17 to the patient thereby to supplement the amount of the ligand or the GPR17; or b) (i) by administering the DNA encoding the GPR17 to the patient and expressing the same, or (ii) by inserting and expressing the DNA encoding the GPR17 in the objective cells and then transplanting the cells to the patient, whereby the activities of the ligand can be sufficiently exhibited.

That is, a) the ligand, b) the GPR17 or c) the DNA encoding the GPR17 is useful as a medicament such as a preventive/therapeutic agent for diseases associated with dysfunction of the ligand or the GPR17.

Specifically, the ligand, the GPR17 or the DNA of the present invention can be used as a low-toxic and safe medicament, for example, as an agent for the prevention/treatment of, e.g., neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

When the ligand or the GPR17 is used as the preventive/therapeutic agent described above, the ligand or the GPR17 can be prepared into a pharmaceutical composition in a conventional manner.

On the other hand, where the DNA of the present invention is used as the preventive/therapeutic agent described above, the DNA of the present invention is administered by itself, alternatively, the DNA is inserted into an appropriate vector such as retrovirus vector, adenovirus vector, adenovirus-associated virus vector, etc. and then administered in a conventional manner. The DNA of the present invention may also be administered as intact DNA, or with auxiliary adjuvants to assist its uptake by gene gun or through a catheter such as a hydrogel catheter.

For example, a) the ligand, b) the GPR17 or c) the DNA of the present invention can be used orally, for example, in the form of tablets which may be sugar coated if necessary, capsules, elixirs, microcapsules etc., or parenterally in the form of injectable preparations such as a sterile solution and a suspension in water or with other pharmaceutically acceptable liquid. These preparations can be manufactured by mixing a) the ligand, b) the GPR17 or c) the DNA of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The effective component in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated by conventional procedures used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate, benzyl alcohol, etc.

The preventive/prophylactic agents described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

Since the thus obtained pharmaceutical preparation is safe and low toxic, the preparation can be administered to human or other mammals (e.g., rats, mice, rabbits, sheep, swine, bovine, cats, dogs, monkeys, etc.).

For example, the dose of the ligand varies depending on subject to be administered, target organ, conditions, method for administration, etc.; in oral administration for the patient (as 60 kg body weight) with, e.g., diabetic polyneuropathy, the dose is normally about 0.1 mg to about 100 mg, preferably about 1.0 to about 50 mg, and more preferably about 1.0 to about 20 mg per day. In parenteral administration, the single dose varies depending on subject to be administered, target organ, conditions, method for administration, etc.; for example, in the form of, e.g., an injectable preparation, it is advantageous for the patient (as 60 kg body weight) with, e.g., diabetic polyneuropathy, to administer the ligand intravenously normally in a daily dose of about 0.01 to about 30 mg, preferably about 0.1 to about 20 mg, and more preferably about 0.1 to about 10 mg. For other animal species, the corresponding dose as converted per 60 kg body weight can be administered.

The dose of the DNA of the present invention varies depending on subject to be administered, target organ, conditions, method for administration, etc.; in oral administration for the patient (as 60 kg body weight) with, e.g., diabetic polyneuropathy, the dose is normally about 0.1 mg to about 100 mg, preferably about 1.0 to about 50 mg, and more preferably about 1.0 to about 20 mg per day. In parenteral administration, the single dose varies depending on subject to be administered, target organ, conditions, method for administration, etc.; for example, in the form of an injection, it is advantageous for the patient (as 60 kg body weight) with, e.g., diabetic polyneuropathy, to administer the DNA intravenously in a daily dose of about 0.01 to about 30 mg, preferably about 0.1 to about 20 mg, and more preferably about 0.1 to about 10 mg. For other animal species, the corresponding dose as converted per 60 kg body weight can be administered.

(2) Gene Diagnostic Agent

By using the DNA and antisense DNA of the present invention as probes, abnormalities (gene abnormalities) of the DNA or mRNA encoding the GPR17 of the present invention or its partial peptides in human or other mammals (e.g., rats, mice, rabbits, sheep, swine, bovine, cats, dogs, monkeys, etc.) can be detected, and the DNA and antisense DNA are thus useful as gene diagnostic agents for the damage against the DNA or mRNA, its mutation, or reduced expression, or an increase or overexpression of the DNA or mRNA.

The gene diagnosis described above using the DNA or antisense DNA of the present invention can be performed by, for example, the publicly known northern hybridization assay or the PCR-SSCP assay (Genomics, 5, 874-879 (1989); Proceedings of the National Academy of Sciences of the United States of America, 86, 2766-2770 (1989)), etc.

Where the reduced expression of the GPR17 is detected, e.g., by northern hybridization or where mutation of DNA is detected by PCR-SSCP, it can be diagnosed that one suffers from, for example, neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.; or it is highly likely to suffer from these disease in the future.

On the other hand, where overexpression of the GPR17 is detected, e.g., by northern hybridization, it can be diagnosed that one suffers from diseases, for example, nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc., or it is highly likely to suffer from these disease in the future.

(3) Medicament Comprising the Compound or its Salt that Alters the Expression Level of the GPR17 of the Present Invention By using the DNA of the present invention as a probe, the DNA can be used for screening the compound or its salt that alters the expression level of the GPR17 of the present invention.

That is, the present invention provides a method of screening the compound or its salt that alters the expression level of the GPR17 of the present invention, which comprises measuring the amount of mRNA for the GPR17 of the present invention contained, for example, in (i) a) blood, b) particular organs, c) tissues or cells isolated from the organs of non-human mammals or in (ii) transformants, etc.

The amount of mRNA of the GPR17 of the present invention can be specifically measured as follows.

(i) Normal or disease models of non-human mammals (e.g., mice, rats, rabbits, sheep, swine, bovine, cats, dogs, monkeys, more specifically, Alzheimer disease model rats, mice, rabbits, etc.) receive administration of a drug (e.g., immunomodulators, etc.) or physical stress (e.g., soaking stress, electric shock, light and darkness, low temperature, etc.), and the blood, particular organs (e.g., brain, liver, kidney, etc.), or tissues or cells isolated from the organs are obtained after a specified period of time. The mRNA of the GPR17 of the present invention contained in the thus obtained cells is extracted from the cells, for example, in a conventional manner and quantified by means of, e.g., TaqMan PCR, or may also be analyzed by northern blot technique by publicly known methods.

(ii) Transformants that express the GPR17 of the present invention are prepared according to the methods described above, and the mRNA encoding the GPR17 of the present invention can be quantified and analyzed, as described above.

The compound or its salt that alters the expression level of the GPR17 of the present invention can be screened by the following procedures.

(i) To normal or disease models of non-human mammals, a test compound is administered at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the amount of mRNA of the GPR17 of the present invention contained in cells are quantified and analyzed.

(ii) Transformants are cultured in a conventional manner and a test compound is mixed in the culture medium. After incubation for a given time period (after 1 day to 7 days, preferably after 1 day to 3 days, more preferably after 2 to 3 days), the amount of mRNA of the GPR17 of the present invention contained in the transformants can be quantified and analyzed.

The test compounds may be peptides, proteins, antibodies, non-peptide compounds, synthetic compounds, fermentation products, cell extract, plant extract, animal tissue extract, plasma. These compounds may be novel or known compounds. The test compounds may form salts and as salts of the test compounds, there are, for example, metal salts, ammonium salts, salts with organic bases, salts with inorganic acids, salts With organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc.

Of these salts, preferred are pharmaceutically acceptable salts. Where the compounds have, for example, acidic functional groups in the compound, the salts include inorganic salts such as alkali metal salts (e.g., sodium salts, potassium salts, etc.), alkaline earth metal salts (e.g., calcium salts, magnesium salts, barium salts, etc.), etc.; ammonium salts, etc.; and where the compounds have basic functional groups in the compound, the salts include salts with inorganic acids such as hydrobromic acid, nitric acid, sulfuric acid, phosphoric acid, etc., or salts with organic acids such as acetic acid, phthalic acid, fumaric acid, oxalic acid, tartaric acid, maleic acid, citric acid, succinic acid, methanesulfonic acid, p-toluenesulfonic acid, etc.

The compound, which is obtained by the screening methods of the present invention, is the compound that alters the expression level of the GPR17 of the present invention. Specifically, it is (i) the compound that increases the expression level of the GPR17 of the present invention thereby to potentiate the GPR17-mediated cell stimulating activities (e.g., activities that promote or suppress arachidonic acid release, acetylcholine release, intracellular $Ca^{2+}$ release, intracellular cAMP production, intracellular cAMP production suppression, intracellular cGMP production, inositol phosphate production, changes in cell membrane potential, phosphorylation of intracellular proteins, activation of c-fos, pH reduction, changes in the expression level of serum responsive factor, changes in localization of the GPR17 in the cell, etc.); and (ii) the compound that decreases the expression level of the GPR17 of the present invention thereby to attenuate the cell-stimulating activities.

The compounds may be peptides, proteins, antibodies, non-peptide compounds, synthetic compounds, fermentation products, cell extracts, plant extracts, animal tissue extracts, plasma, etc. and may be novel compounds or known compounds. As salts of the test compounds, there are, for example, metal salts, ammonium salts, salts with organic bases, salts with inorganic acids, salts with organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc.

Of these salts, preferred are pharmaceutically acceptable salts. Where the compounds have, for example, acidic functional groups in the compound, the salts include inorganic salts such as alkali metal salts (e.g., sodium salts, potassium salts, etc.), alkaline earth metal salts (e.g., calcium salts, magnesium salts, barium salts, etc.), etc.; ammonium salts, etc.; and where the compounds have basic functional groups in the compound, the salts include salts with inorganic acids such as hydrobromic acid, nitric acid, sulfuric acid, phosphoric acid, etc., or salts with organic acids such as acetic acid, phthalic acid, fumaric acid, oxalic acid, tartaric acid, maleic acid, citric acid, succinic acid, methanesulfonic acid, p-toluenesulfonic acid, etc.

The compounds obtained by the screening methods described above include: (i) compounds that increase the expression level of the GPR17 of the present invention to exhibit the effects of preventing/treating diseases associated with dysfunction of the GPR17 of the present invention, for example, neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.; or, (ii) compounds that decrease the expression level of the GPR17 of the present invention to exhibit the effects of preventing/treating diseases caused by the overexpression of the GPR17 of the present invention, for example, nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), or the like.

Therefore, the compounds or salts thereof increasing the expression level of the GPR17 of the present invention, which are obtained by the screening methods described above, can be used as low-toxic and safe medicaments, for example, as agents for the prevention/treatment of, e.g., neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

On the other hand, the compounds or salts thereof decreasing the expression level of the GPR17 of the present invention, which are obtained by the screening methods described above, can be used as low-toxic and safe medicaments, for example, as agents for the prevention/treatment of diseases caused by the overexpression of the GPR17 of the present invention, e.g., nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

Where the compound or its salt, which is obtained by the screening methods of the present invention, is used as a pharmaceutical composition, the compound or its salt can be formed into a pharmaceutical preparation in a conventional manner.

For example, the compound can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, which can be used in combination with a dissolution aid such as benzyl benzoate, benzyl alcohol, etc.

Furthermore, the preventive/therapeutic agents described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic and can be administered to human or mammals (e.g., rats, mice, rabbits, sheep, swine, bovine, cats, dogs, monkeys, etc.).

The dose of the compound or its salt varies depending on subject to be administered, target organ, conditions, method for administration, etc.; in oral administration, the compound that increases the expression level of the GPR17 of the present invention is administered to the patient (as 60 kg body weight) with, e.g., diabetic polyneuropathy is normally about 0.1 mg to about 100 mg, preferably about 1.0 to about 50 mg, and more preferably about 1.0 to about 20 mg per day. In parenteral administration, the single dose may vary depending on subject to be administered, target organ, conditions, method for administration, etc. and in the form of, e.g., an injectable preparation, the compound that increases the expression level of the GPR17 of the present invention is advantageously administered intravenously to the patient (as 60 kg body weight) with, e.g., diabetic polyneuropathy normally in a daily dose of about 0.01 to about 30 mg, preferably about 0.1 to about 20 mg, and more preferably about 0.1 to about 10 mg. For other animal species, the corresponding dose as converted per 60 kg body weight can be administered.

(4) Method for Diagnosis Using the Antibody of the Present Invention

The antibody to the ligand peptide is capable of specifically recognizing the ligand peptide of the present invention and can be used for detection or neutralization of the ligand peptide in a test fluid.

The antibody to the GPR17 of the present invention is capable of specifically recognizing the GPR17 of the present invention and can be used for detection or neutralization of the GPR17 in a test fluid.

Hereinafter the method for quantification of the GPR17 using the antibody to the GPR17 of the present invention will be described, and the method for quantification of the ligand peptide using the antibody to the ligand peptide can be carried out as well.

That is, the present invention provides, for example, the following quantification methods:

(i) a method for quantification of the GPR17 in a test fluid, which comprises competitively reacting the antibody of the present invention with the test fluid and a labeled form of the GPR17, and measuring a ratio of the labeled GPR17 bound to the antibody; and, (ii) a method for quantification of the GPR17 in a test fluid, which comprises reacting the test fluid with the antibody of the present invention immobilized on a carrier and a labeled form of another antibody of the present invention simultaneously or sequentially, and measuring the activity of the label on the immobilized carrier.

In the quantification method (ii) described above, it is preferred that one antibody recognizes the N-terminal region of the GPR17, and another antibody reacts with the C-terminal region of the GPR17.

Using the monoclonal antibodies to the GPR17, the GPR17 can be quantified. In addition, the GPR17 can also be detected by tissue staining or the like. For these purpose, the antibody molecule itself may be used, or $F(ab')_2$, Fab' or Fab fraction of the antibody molecule may also be used.

The quantification methods of the GPR17 using the antibodies of the present invention are not particularly limited. Any quantification method can be used, so long as the amount of antibody, antigen, or antibody-antigen complex corresponding to the amount of antigen (e.g., the amount of the GPR17) in the test fluid can be detected by chemical or physical means and the amount of the antigen can be calculated from a standard curve prepared from standard solutions containing known amounts of the antigen. For example, nephrometry, competitive methods, immunometric method, and sandwich method are appropriately used, with the sandwich method described below being most preferable in terms of sensitivity and specificity.

As the labeling agent for the methods using labeled substances, there are employed, for example, radioisotopes, enzymes, fluorescent substances, luminescent substances, etc. For the radioisotope, for example, [$^{125}$I], [$^{131}$I]. [$^{3}$H], [$^{14}$C] and the like are used. As the enzyme described above, stable enzymes with high specific activity are preferred; for example, β-galactosidase, β-glucosidase, alkaline phosphatase, peroxidase, malate dehydrogenase and the like are used. Examples of the fluorescent substance used are fluorescamine and fluorescein isothiocyanate are used. For the luminescent substance, there are used, for example, luminol, luminol derivatives, luciferin, and lucigenin. Furthermore, the biotin-avidin system may be used for binding antibody or antigen to the label.

For immobilization of antigen or antibody, physical adsorption may be used. Chemical binding methods conventionally used for insolubilization or immobilization of the GPR17, enzymes or the like may also be used. For the carrier, for example, insoluble polysaccharides such as agarose, dextran, cellulose, etc.; synthetic resin such as polystyrene, polyacrylamide, silicon, etc., and glass or the like are used.

In the sandwich method, the immobilized monoclonal antibody of the present invention is reacted with a test fluid (primary reaction), then with the labeled monoclonal antibody of the present invention (secondary reaction), and the activity of the label on the immobilizing carrier is measured, whereby the amount of the GPR17 of the present invention in the test fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the methods of assaying the GPR17 by the sandwich method according to the present invention, antibodies that bind to different sites of the GPR17 are preferably used as the monoclonal antibodies of the present invention for the primary and secondary reactions. That is, in the antibodies used for the primary and secondary reactions are, for example, when the antibody used in the secondary reaction recognizes the C-terminal region of the GPR17, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, competitive method, immunometric method, nephrometry, etc.

In the competitive method, antigen in a test fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying these individual immunological methods to the quantification methods of the present invention, any particular conditions or procedures are not required. Systems for measuring the GPR17 of the present invention are constructed by adding the usual technical consideration in the art to the conventional conditions and procedures. For the details of these general technical means, reference can be made to the following reviews and texts.

For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing).

As described above, the GPR17 of the present invention can be quantified with high sensitivity by using the antibodies of the present invention.

Furthermore, when a change in the GPR17 level is detected by quantifying the GPR17 level using the antibody of the present invention, it can be diagnosed that one suffers from disease, e.g., neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.; or it is highly likely for one to suffer from these disease in the future.

(5) Methods for Screening Agonists for the GPR17

The ligand binds to the GPR17, whereby an increased gene expression of serum responsive factor or changes in internalization of the GPR17 protein is observed. Thus, the GPR17 is useful as a reagent for searching or identifying agonists (including naturally occurring ligands and synthetic ligands) for the GPR17 other than the ligand described above, using these changes as an indicator.

That is, the present invention provides a method of determining the agonist for the GPR17, which comprises assaying the GPR17-mediated cell-stimulating activities (e.g., activities that promote or suppress arachidonic acid release, acetylcholine release, intracellular $Ca^{2+}$ release, intracellular cAMP production, intracellular cAMP production suppression, intracellular cGMP production, inositol phosphate production, changes in cell membrane potential, phosphorylation of intracellular proteins, activation of c-fos, pH reduction, changes in the expression level of serum responsive factor, changes in internalization of the GPR17, etc.), particularly, an intracellular cAMP production suppressing activity, when a test compound is brought in contact with a cell containing the GPR17.

Examples of test compounds include publicly known ligands (for example, angiotensin, bombesin, canavinoid, cholecystokinin, glutamine, serotonin, melatonin, neuropeptide Y, opioids, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, the chemokine superfamily (e.g., the CXC chemokine subfamily such as IL-8, GROα, GROβ, GROγ, NAP-2, ENA-78, GCP-2, PF4, IP-10, Mig, PBSF/SDF-1, etc.; the CC chemokine subfamily such as MCAF/MCP-1, MCP-2, MCP-3, MCP-4, eotaxin, RANTES, MIP-1=, MIP-1β, HCC-1, MIP-3α/LARC, MIP-3β/ELC, I-309, TARC, MIPF-1, MIPF-2/eotaxin-2, MDC, DC-CK1/PARC, SLC, etc.; the C chemokine subfamily such as lymphotactin, etc.; the CX3C chemokine subfamily such as fractalkine, etc.), endothelin, enterogastrin, histamine, neurotensin, TRH, pancreatic polypeptide, galanin, lysophosphatidic acid (LPA), sphingosine 1-phosphate, etc.) as well as other substances, for example, tissue extracts, cell culture supernatants from humans or mammals (e.g., mice, rats, swine, bovine, sheep, monkeys, etc.) or low molecular synthetic compound. For example, the tissue extract, or cell culture supernatant, is added to the GPR17 while assaying the cell-stimulating activities and fractionating to finally obtain a single ligand.

(6) Method of Screening a Compound (Agonist, Antagonist, etc.) or its Salt that Alters the Binding Properties of the GPR17 of the Present Invention to its Ligand, and Medicaments Comprising the Compound or its Salt that Alters the Binding Properties of the GPR17 of the Present Invention to its Ligand By using the GPR17 of the present invention, or by constructing a recombinant GPR17 expression system and using the receptor-binding assay system using the expression system, the compound (e.g., peptide, protein, antibody, a non-peptide compound, a synthetic compound, a fermentation product, a cell extract, a plant extract, an animal tissue extract, plasma, etc.) or salts thereof that alter the binding properties of the ligand to the GPR17 of the present invention can be screened efficiently.

Examples of these compounds include (a) a compound showing the GPR17-mediated cell stimulating activities (a so-called agonist for the GPR17 of the present invention), (b) a compound that inhibits the GPR17-mediated cell stimulating activities (a so-called antagonist to the GPR17 of the present invention), (c) a compound that potentiates the binding affinity of the ligand to the GPR17 of the present invention, or (d) a compound that decreases the binding affinity of the ligand to the GPR17 of the present invention, and the like.

The cell stimulating activities include, for example, activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, elevation of gene expression of serum responsive factor, changes in localization of the GPR17 protein, etc.; among them, the activity of elevation of gene expression of serum responsive factor and the suppression of cAMP production are particularly preferred.

That is, the present invention provides a method of screening a compound or its salt that alters the binding properties of the GPR17 of the present invention to the ligand, which comprises comparing the following two cases: (i) the case wherein the GPR17 of the present invention is brought in contact with the ligand; and (ii) the case wherein the GPR17 of the present invention is brought in contact with the ligand and a test compound.

The screening methods of the present invention is characterized by determining and comparing, for example, the binding amounts of the ligand to the GPR17, the cell stimulating activities, etc. between the cases (i) and (ii).

As the ligand, there can be used, instead of the ligand described above, the compound or its salt that alters the binding properties of the ligand to the GPR17 of the present invention (e.g., a low molecular weight synthetic compound, preferably a low molecular synthetic agonist). The compound or its salt that alters the binding properties of the ligand to the GPR17 of the present invention can be obtained using the screening methods later described. In the screening methods of the present invention, the compounds or salts thereof that alter the binding properties of these ligands to the GPR17 of the present invention are also referred to as the ligand.

More specifically, the present invention provides cell stimulation assay systems, including the following methods.

a) A method of screening a compound or its salt that alters the binding properties of the ligand to the GPR17 of the present invention, which comprises measuring the binding amount of a ligand to the GPR17 in the case wherein the ligand is brought in contact with the GPR17 of the present invention and in the case wherein the ligand and a test compound are brought in contact with the GPR17 of the present invention, and comparing the binding amounts.

b) A method of screening a compound or its salt that alters the binding properties of the ligand to the GPR17 of the present invention, which comprises measuring the binding amount of a ligand to a cell containing the GPR17 of the present invention or a membrane fraction of the cell, in the case wherein the ligand is brought in contact with the cell or the membrane fraction and in the case wherein the ligand and a test compound are brought in contact with the cell containing the GPR17 of the present invention or its membrane fraction, and comparing the binding amounts.

c) A method of screening a compound or its salt that alters the binding properties of the ligand to the GPR17, which comprises measuring the amount of ligand bound to the GPR17 of the present invention, in the case wherein the ligand is brought in contact with the GPR17 of the present invention expressed on a cell membrane by culturing a transformant containing the DNA of the present invention and in the case wherein the ligand and a test compound are brought in contact with the GPR17 of the present invention expressed on the cell membrane by culturing a transformant containing the DNA of the present invention, and comparing the cases.

(d) The screening method according to (a)-(c) describe above, wherein the ligand is a labeled ligand.

(e) A method of screening a compound or its salt that alters the binding properties of the ligand to the GPR17 of the present invention, which comprises assaying the GPR17-mediated cell stimulating activities, in the case wherein a compound (e.g., the ligand to the GPR17 of the present invention, etc.) that activates the GPR17 of the present invention is brought in contact with a cell containing the GPR17 of the present invention and in the case wherein said compound that activates the GPR17 of the present invention and a test compound are brought in contact with the cell containing the GPR17 of the present invention, and comparing the cell stimulating activities between the two cases.

(f) A method of screening a compound or its salt that alters the binding properties of the ligand to the GPR17 of the present invention, which comprises assaying the receptor protein-mediated cell stimulating activities in the case wherein a compound (e.g., the ligand to the GPR17 of the present invention, etc.) that activates the GPR17 of the present invention is brought in contact with the GPR17 of the present invention expressed on a cell membrane by culturing a transformant containing the DNA of the present invention and in the case wherein said compound that activates the GPR17 of the present invention and a test compound are brought in contact with the GPR17 of the present invention expressed on a cell membrane by culturing a transformant containing the DNA of the present invention, and comparing the cell stimulating activities.

Hereinafter the screening methods of the present invention will be described more specifically.

First, the GPR17 of the present invention, which is used for the screening methods of the present invention, may be any one so long as it contains the GPR17 of the present invention described above, though membrane fractions from mammalian organs containing the GPR17 of the present invention are preferably employed. Since it is very difficult to obtain human-derived organs especially, the human-derived GPR17, etc. expressed abundantly by use of recombinants are suitable for use in the screening.

To produce the GPR17 of the present invention, the methods described above can be used, and the DNA of the present invention is preferably expressed on mammalian cells or insect cells. As the DNA fragment encoding the target protein region, a complementary DNA may be used but is not limited thereto. For example, gene fragments or a synthetic DNA may also be used. In order to introduce the DNA fragment encoding the GPR17 of the present invention into host animal cells and express the same efficiently, the DNA fragment is preferably incorporated into a polyhedron promoter of nuclear polyhedrosis virus (NPV) belonging to the Baculovirus whose host is insects, an SV40-derived promoter, a promoter of retrovirus, a metallothionein promoter, a human heat shock promoter, a cytomegalovirus promoter, SRα promoter, etc. at the downstream thereof. The quantity and quality of the thus expressed receptors can be examined by a publicly known method, for example, by the method described in the literature [Nambi, P. et al., J. Biol. Chem., 267, 19555-19559, 1992].

Accordingly, in the screening methods of the present invention, the substance containing the GPR17 of the present invention may be GPR17 purified by publicly known methods, or a cell containing said GPR17 or a membrane fraction of the cell containing said GPR17 may be used as well.

When the cell containing the GPR17 of the present invention is used in the screening methods of the present invention, the cell may be fixed with glutaraldehyde, formalin, etc. The fixation may be carried out by a publicly known method.

The cell containing the GPR17 of the present invention refers to a host cell in which the GPR17 is expressed. Preferred examples of such a host cell include *Escherichia coli*, *Bacillus subtilis*, yeast, insect cells, animal cells, etc.

The membrane fraction of the cell means a fraction abundant in cell membrane obtained by cell disruption and subsequent fractionation by publicly known methods. Cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the GPR17 expressed and membrane components such as cell-derived phospholipids, membrane proteins, etc.

The amount of the GPR17 in a cell containing said GPR17 or the cell membrane fraction is preferably $10^3$ to $10^8$ molecules per cell, more preferably $10^5$ to $10^7$ molecules per cell. As the level of expression increases, the ligand binding activity per unit of membrane fraction (specific activity) increases so that not only the highly sensitive screening system can be constructed but also large quantities of samples can be assayed with the same lot.

To perform (a) through (d) above for screening the compound that alters the binding properties of the ligand to the GPR17 of the present invention, an appropriate fraction of the GPR17 and a labeled form of the ligand are required. For the GPR17 fraction, a naturally occurring GPR17 fraction or a recombinant GPR17 fraction having activities equivalent thereto. Herein, the equivalent activities refer to ligand binding activities, signal transduction activities, etc., which are equivalent. As the labeled ligand, there are employed, for example, ligands labeled with, e.g., [$^3$H], [$^{125}$I], [$^{14}$C], [$^{35}$S], etc.

More specifically, for screening the compound that alters the binding properties of the ligand to the GPR17 of the present invention, a GPR17 preparation is prepared by suspending cells containing the GPR17 of the present invention or a membrane fraction of the cells in a buffer appropriate for use in the screening methods. Any buffer can be used so long as it does not interfere the ligand-GPR17 binding, including a phosphate buffer or a Tris-HCl buffer, having pH of 4 to 10 (preferably pH of 6 to 8), etc. For the purpose of minimizing non-specific binding, a surfactant such as CHAPS, Tween-80™ (Kao-Atlas Inc.), digitonin, deoxycholate, etc., may optionally be added to the buffer. Further for the purpose of suppressing the degradation of the receptor or ligand with a protease, a protease inhibitor such as PMSF, leupeptin, E-64 (manufactured by Peptide Institute, Inc.), pepstatin, etc. may also be added. A given amount (5,000 cpm to 500,000 cpm) of a labeled form of the ligand is added to 0.01 ml to 10 ml of the receptor protein solution, in which $10^{-4}$ M to $10^{-10}$ M of a test compound is co-present. To determine the amount of non-specific binding (NSB), a reaction tube charged with an unlabeled form of the ligand in a large excess is also provided. The reaction is carried out at approximately 0° C. to 50° C., preferably 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$-NSB) is made 100%, the test compound showing the specific binding amount (B-NSB) of, e.g., 50% or less may be selected as a candidate compound.

To perform the methods (e)-(f) described above for screening the compound or its salt that alters the binding properties of the ligand to the GPR17 of the present invention, for example, the GPR17-mediated cell stimulating activities can be assayed by a publicly known method, or using an assay kit commercially available.

Specifically, the cells containing the GPR17 of the present invention are first cultured in a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., arachidonic acid, cAMP, etc.) due to a degrading enzyme contained in the cells, an inhibitor against such as a degrading enzyme may be added prior to the assay. For detecting the activities such as the cAMP production suppression activity, the baseline production in the cells is increased by forskolin or the like and the suppressing effect on the increased baseline production can be detected.

For the screening through the assay for the cell stimulating activities, cells expressing an appropriate GPR17 are required. Preferred cells expressing the GPR17 of the present invention are a cell line having the GPR17 of the present invention of naturally occurring type and the aforesaid cell line, in which the recombinant GPR17 described above has been expressed, etc.

Examples of the test compounds include peptides, proteins, antibodies, non-peptide compounds, synthetic compounds, fermentation products, cell extracts, plant extracts, animal tissue extracts, plasma, etc. These compounds may be either novel compounds or publicly known compounds. The test compounds may form salts and as salts of the test compounds, there are, for example, metal salts, ammonium salts, salts with organic bases, salts with inorganic acids, salts with organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc.

Of these salts, preferred are pharmaceutically acceptable salts. Where the compounds have, for example, acidic functional groups, the salts include inorganic salts such as alkali metal salts (e.g., sodium salts, potassium salts, etc.), alkaline earth metal salts (e.g., calcium salts, magnesium salts, barium salts, etc.), etc.; ammonium salts, etc.; and where the compounds have basic functional groups, the salts include salts with inorganic acids such as hydrobromic acid, nitric acid, sulfuric acid, phosphoric acid, etc., or salts with organic acids such as acetic acid, phthalic acid, fumaric acid, oxalic acid, tartaric acid, maleic acid, citric acid, succinic acid, methanesulfonic acid, p-toluenesulfonic acid, etc. The test compound which is preferably used is a compound designed to bind to the ligand-binding pocket, based on the atomic coordinate and the position of the ligand-binding pocket in the active site of the GPR17 of the present invention. The atomic coordinate and the position of the ligand-binding pocket in the active site of the GPR17 of the present invention can be determined by publicly known methods or modifications thereof.

The kit for screening the compound or its salt that alters the binding properties of the ligand to the GPR17 of the present invention is a kit comprising the GPR17 of the present invention, a cell containing the GPR17 of the present invention, or a membrane fraction of the cell containing the GPR17 of the present invention, and the like.

Examples of the screening kit of the present invention include the following.

1. Reagent for Screening a) Assay Buffer and Wash Buffer

Hanks' balanced salt solution (manufactured by Gibco, Inc.) supplemented with 0.05% bovine serum albumin (manufactured by Sigma, Inc.)

The solution is sterilized by filtration through a 0.45 μm filter, and stored at 4° C. or may be prepared at use.

b) GPR17 Preparation

CHO cells wherein the GPR17 of the present invention has been expressed are passaged in a 12-well plate at a density of $5\times10^5$ cells/well followed by culturing at 37° C. under 5% $CO_2$ and 95% air for 2 days.

c) Labeled Ligand

An aqueous solution of the ligand labeled with commercially available [$^3$H], [$^{125}$I], [$^{14}$C], [$^{35}$S], etc. is stored at 4° C. or −20° C., and diluted to 1 μM with the assay buffer upon use.

d) Standard Ligand Solution

The ligand is dissolved in and adjusted to 1 mM with PBS containing 0.1% bovine serum albumin (manufactured by Sigma, Inc.) and stored at −20° C.

2. Assay Method a) CHO cells wherein the GPR17 of the present invention has been expressed are cultured in a 12-well culture plate and washed twice with 1 ml of the assay buffer, and 490 μl of the assay buffer is added to each well.

b) After adding 5 μl of $10^{-3}$-$10^{-10}$ M test compound solution, 5 μl of labeled ligand is added to the mixture, and the cells are incubated at room temperature for an hour. To determine the amount of the non-specific binding, 5 μl of $10^{-3}$ M ligand is added in place of the test compound.

c) The reaction solution is removed, and the wells are washed 3 times with the washing buffer. The labeled ligand bound to the cells is dissolved in 0.2N NaOH-1% SDS, and mixed with 4 ml of liquid scintillator A (manufactured by Wako Pure Chemical Industries, Ltd.)

d) The radioactivity is measured using a liquid scintillation counter (manufactured by Beckman Co.), and the percent maximum binding (PMB) is calculated by the equation below.

$$PMB=[(B-NSB)/(B_0-NSB)]\times 100$$

PMB: Percent maximum binding

B: Value obtained in the presence of a test compound

NSB: Non-specific binding $B_0$: Maximum binding

A specific procedure to assess if a compound is an agonist/antagonist of the GPR17 may involve (i) or (ii) below.

(i) Binding assay as given for the screening methods a) to c) described above is performed to obtain a compound that alters the binding properties (especially inhibits the binding) of the ligand peptide to the GPR17 of the present invention. Then, it is determined if the compound has the cell stimulating activities described above. The compound or its salt, which has the cell stimulating activities is an agonist for the GPR17 of the present invention, whereas the compound or its salt having no such activities is an antagonist to the GPR17 of the present invention.

(ii) (a) A test compound is brought in contact with a cell containing the GPR17 of the present invention and the cell stimulating activities described above are assayed. The compound or its salt having the cell stimulating activities is an agonist for the GPR17 of the present invention.

(b) The cell stimulating activities mediated by the GPR17 of the present invention are assayed and compared between the case where the compound (e.g., the ligand) that activates the GPR17 of the present invention is brought in contact with a cell containing the GPR17 of the present invention and the case where the compound that activates the GPR17 of the present invention and a test compound are brought in contact with a cell containing the GPR17 of the present invention. The compound or its salt that can decrease the cell stimulating activities by the compound activating the GPR17 of the present invention is an antagonist to the GPR17 of the present invention.

The compound or its salt, which is obtained by using the screening methods or the screening kits of the present invention, is the compound that alters the binding properties of the ligand to the GPR17 of the present invention. Specifically, the compound is: (1) a compound having the cell-stimulating activities mediated by the receptor (a so-called agonist for the GPR17 of the present invention); (2) a compound having the binding activity to the receptor but no cell stimulating activity (a so-called antagonist to the GPR17 of the present invention); (3) a compound that potentiates the binding affinity of the ligand to the GPR17 of the present invention; or (4) a compound that reduces the binding affinity of the ligand to the GPR17 of the present invention.

These compounds may be peptides, proteins, antibodies, non-peptide compounds, synthetic compounds, fermentation products, cell extracts, plant extracts, animal tissue extracts, plasma, etc. These compounds may be novel compounds or known compounds.

Since the agonists for the GPR17 of the present invention have the same physiological activities as the ligand has, the agonists are useful as safe and low toxic medicaments, correspondingly to the physiological activities possessed by the ligand peptide.

The antagonists to the GPR17 of the present invention can suppress the physiological activities the ligand possesses, and are useful as safe, low toxic medicaments to suppress the physiological activities of the ligand peptide.

The compound that potentiates the binding affinity of the ligand to the GPR17 of the present invention is useful as a safe and low toxic medicament to potentiate the physiological activities possessed by the ligand.

The compound that reduces the binding affinity of the ligand to the GPR17 of the present invention is useful as a safe and low toxic medicament to reduce the physiological activities of the ligand thereby to suppress the physiological activities of the ligand possessed by the ligand.

Specifically, the compound or its salt, which is obtained by using the screening methods or screening kits of the present invention, the ligand, the agonist, the compound or its salt that potentiates the binding affinity of the ligand to the GPR17 of the present invention, etc. can be used as a low-toxic and safe medicament, for example, as an agent for the prevention/treatment of, e.g., neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

On the other hand, the antagonist or the compound or its salt that decreases the binding affinity of the ligand to the GPR17 of the present invention, which is obtained by using the screening methods described above, can be used as a low-toxic and safe medicament, for example, as an agent for the prevention/treatment of, e.g., nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), or the like.

Where the compound or its salt, which is obtained by using the screening methods or screening kits of the present invention, is used as the pharmaceutical composition described above, the compound or its salt can be prepared into a pharmaceutical preparation in a conventional manner.

For example, the compound can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, and may be used in combination with a dissolution aid such as benzyl benzoate, benzyl alcohol, etc.

Furthermore, the preventive/therapeutic agents described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic and can be administered to human or mammals (e.g., rats, mice, rabbits, sheep, swine, bovine, cats, dogs, monkeys, etc.).

The dose of the compound or its salt may vary depending on subject to be administered, target organ, conditions, method for administration, etc.; in oral administration, the agonist is administered to the patient (as 60 kg body weight) with, e.g., diabetic polyneuropathy is normally about 0.1 mg to about 100 mg, preferably about 1.0 to about 50 mg, and more preferably about 1.0 to about 20 mg per day. In parenteral administration, the single dose may vary depending on subject to be administered, target organ, conditions, method for administration, etc. and in the form of, e.g., an injectable preparation, the agonist is advantageously administered intravenously to the patient (as 60 kg body weight) with, e.g., diabetic polyneuropathy normally in a daily dose of about 0.01 to about 30 mg, preferably about 0.1 to about 20 mg, and more preferably about 0.1 to about 10 mg. For other animal species, the corresponding dose as converted per 60 kg body weight can be administered. In oral administration, the antagonist is administered to the patient (as 60 kg body weight) with, e.g., Parkinson's disease is normally about 0.1 mg to about 100 mg, preferably about 1.0 to about 50 mg, and more preferably about 1.0 to about 20 mg per day. In parenteral administration, the single dose may vary depending on subject to be administered, target organ, conditions, method for administration, etc. and in the form of, e.g., an injectable preparation, the agonist is administered intravenously to the patient (as 60 kg body weight) with, e.g., Parkinson's disease normally in a daily dose of about 0.01 to about 30 mg, preferably about 0.1 to about 20 mg, and more preferably about 0.1 to about 10 mg. For other animal species, the corresponding dose as converted per 60 kg body weight can be administered.

(7) Methods for Elucidation of the Action Mechanism of Various Drugs

By using the GPR17, it can be confirmed whether or not various drugs exhibit their pharmacological effects mediated by the GPR17.

That is, the present invention provides the following methods.

(1) A method of confirmation that an agent for the prevention/treatment of, e.g., neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc. binds to said receptor protein or a salt thereof, which comprises using the GPR17.

(2) A method of confirmation that an agent for the prevention/treatment of, e.g., neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), etc. is an agonist for said receptor protein or its salt, which comprises using the GPR17.

(3) A method of confirmation that an agent for the prevention/treatment of, e.g., neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc. is an antagonist to said receptor protein or its salt, which comprises using the GPR17.

(4) The screening method according to (1) through (3), wherein the binding amount of each agent to the GPR17 is measured when the agent is brought in contact with the GPR17.

This confirmation method can be performed by using the agent described above in place of the test compound in the aforesaid methods of screening the compound that alters the binding properties of the ligand to the GPR17.

The kit used for the confirmation methods of the present invention comprises the agent described above in place of the test compound, in the aforesaid kits for screening the compound that alters the binding properties of the ligand to the GPR17.

By using the confirmation methods of the present invention as described above, it can be confirmed that various drugs commercially available or under development exhibit the GPR17-mediated pharmacological effects.

(8) Medicament Comprising the Compound or its Salt that Alters the Amount of the GPR17 of the Present Invention or its Partial Peptide in Cell Membrane The antibody of the present invention is capable of specifically recognizing the GPR17 of the present invention and can be used for screening the compound or its salt that alters the amount of the GPR17 of the present invention in the cell membrane.

That is, the present invention provides, for example, the following methods:

(i) a method of screening the compound or its salt that alters the amount of the GPR17 of the present invention in the cell membrane, which comprises quantifying the GPR17 of the present invention contained in a cell membrane fraction isolated after disrupting a) blood, b) a particular organ or c) tissues or cells isolated from the organ of non-human mammal;

(ii) a method of screening the compound or its salt that alters the amount of the GPR17 of the present invention in the cell membrane, which comprises disrupting transformants, etc. expressing the GPR17 of the present invention, isolating the cell membrane fraction and quantifying the GPR17 of the present invention contained in the cell membrane fraction;

(iii) a method of screening the compound or its salt that alters the amount of the GPR17 of the present invention in the cell membrane, which comprises preparing a slice of a) blood, b) a particular organ or c) tissues or cells, etc. isolated from the organ of non-human mammal and quantifying the staining intensity of said receptor protein on the cell surface using immunostaining assay thereby to confirm said protein on the cell membrane; and, (iv) a method of screening the compound or its salt that alters the amount of the GPR17 of the present invention in the cell membrane, which comprises preparing a slice of a transformant expressing the GPR17 of the present invention and quantifying the staining intensity of said receptor protein on the cell surface using immunostaining assay thereby to confirm said protein on the cell membrane.

Specifically, the GPR17 of the present invention contained in the cell membrane fraction can be quantified as follows.

(i) Normal or disease models of non-human mammals (e.g., mice, rats, rabbits, sheep, swine, bovine, cats, dogs, monkeys, more specifically, Alzheimer disease model rats, mice, rabbits, etc.) are administered with drugs (e.g., immunomoderators, etc.) or physical stress (e.g., soaking stress, electric shock, light and darkness, low temperature, etc.), and the blood, particular organs (e.g., brain, liver, kidney, etc.), or tissues or cells isolated from the organs are obtained after a specified period of time. The obtained organs, tissues, cells or the like are suspended in, for example, an appropriate buffer (e.g., Tris hydrochloride buffer, phosphate buffer, HEPES buffer, etc.), and the organs, tissues or cells are disrupted, and the cell membrane fraction is obtained using surfactants (e.g., Triton-X 100™, Tween 20™) and further using techniques such as centrifugal separation, filtration, column fractionation, etc.

The cell membrane fraction means a fraction abundant in cell membrane obtained by cell disruption and subsequent fractionation by publicly known methods. Cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in GPR17 expressed and membrane components such as cell-derived phospholipids, membrane proteins, etc.

The GPR17 of the present invention contained in the cell membrane fraction can be quantified by, for example, the sandwich immunoassay, western blot analysis, etc. using the antibody of the present invention.

The sandwich immunoassay can be performed as described above, and the western blot can be performed by publicly known methods.

(ii) Transformants expressing the GPR17 of the present invention are prepared by the method described above, and the GPR17 of the present invention contained in the cell membrane fraction can be quantified.

The compound or its salt that alters the amount of the GPR17 of the present invention in cell membranes can be screened as follows.

(i) Normal or disease models of non-human mammals are administered with a test compound at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the amount of the GPR17 of the present invention in the cell membranes can be quantified.

(ii) Transformants are cultured in a conventional manner and a test compound is mixed in the culture medium. After a specified time (after 1 day to 7 days, preferably after 1 day to 3 days, more preferably after 2 to 3 days), the amount of the GPR17 of the present invention in the cell membranes can be quantified.

Specifically, the GPR17 of the present invention contained in cell membrane fractions is confirmed as follows.

(iii) Normal or disease models of non-human mammals (e.g., mice, rats, rabbits, sheep, swine, bovine, cats, dogs, monkeys, etc., more specifically, Alzheimer disease model rats, mice, rabbits, etc.) are administered with drugs (e.g., immunomoderators, etc.) or physical stress (e.g., soaking stress, electric shock, light and darkness, low temperature, etc.) or the like, and blood or particular organ (e.g., brain, liver, kidney, etc.), or the tissues or cells isolated from the organ are obtained after a specified period of time. Tissue sections are prepared from the thus obtained organs, tissues, cells, etc. in a conventional manner followed by immunostaining with the antibody of the present invention. The staining intensity of said receptor protein on the cell surface is quantified to confirm said protein on the cell membrane, whereby the amount of the GPR17 of the present invention on the cell membrane can be confirmed quantitatively or qualitatively.

(iv) The confirmation can also be made in a similar manner, using transformants or the like, which express the GPR17 of the present invention.

The compounds or their salts obtained by the screening methods of the present invention are compounds that have the action of changing the amount of the GPR17 of the present invention in cell membranes. Specifically, these compounds are: (1) compounds that increase the amount of the GPR17 of the present invention in cell membranes thereby to potentiate the GPR17-mediated cell stimulating activities (the activities that promote or suppress arachidonic acid release, acetylcholine release, intracellular $Ca^{2+}$ release, intracellular cAMP production, intracellular cAMP production suppression, intracellular cGMP production, inositol phosphate production, changes in cell membrane potential, phosphorylation of intracellular proteins, activation of c-fos, pH reduction, elevation of gene expression of serum responsive factor, changes in localization of the GPR17 protein, etc.) and (2) compounds that decrease the amount of the GPR17 of the present invention in the cell membranes thereby to attenuate the cell stimulating activities.

The compounds may be peptides, proteins, antibodies, non-peptide compounds, synthetic compounds, fermentation products, cell extracts, plant extracts, animal tissue extracts, plasma, etc. These compounds may be novel compounds or publicly known compounds.

Examples of salts of these compounds include metal salts, ammonium salts, salts with organic bases, salts with inorganic acids, salts with organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc. Of these salts, preferred are pharmaceutically acceptable salts. Where the compounds have, for example, acidic functional groups, the salts include inorganic salts such as alkali metal salts (e.g., sodium salts, potassium salts, etc.), alkaline earth metal salts (e.g., calcium salts, magnesium salts, barium salts, etc.), etc.; ammonium salts, etc.; and where the compounds have basic functional groups, the salts include salts with inorganic acids such as hydrobromic acid, nitric acid, sulfuric acid, phosphoric acid, etc., or salts with organic acids such as acetic acid, phthalic acid, fumaric acid, oxalic acid, tartaric acid, maleic acid, citric acid, succinic acid, methanesulfonic acid, p-toluenesulfonic acid, etc.

The compound or its salt that increases the amount of the GPR17 of the present invention in cell membranes thereby to potentiate the cell-stimulating activities can be used as a medicament, e.g., as an agent for the prevention/treatment of diseases associated with dysfunction of the GPR17 of the present invention. Specifically, the compound or its salt can be used as a low-toxic and safe medicament, e.g., as an agent for the prevention/treatment of neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

The compound or its salt that decreases the amount of the GPR17 of the present invention in cell membranes thereby to attenuate the cell-stimulating activities is useful as a safe and low toxic agent for the prevention/treatment of, for example, nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

Where the compound or its salt obtained by using the screening methods of the present invention is used as a pharmaceutical composition, the compound or its salt can be prepared into a pharmaceutical preparation in a conventional manner. For example, the compound or its salt can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound or its salt, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, which can be used in combination with a dissolution aid such as benzyl benzoate, benzyl alcohol, etc.

In addition, the preventive/therapeutic agent described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The thus obtained pharmaceutical preparation is safe and low toxic and can be administered to, e.g., human or mammals (e.g., rats, mice, rabbits, sheep, swine, bovine, cats, dogs, monkeys, etc.).

The dose of the compound or its salt may vary depending on subject to be administered, target organ, conditions, method for administration, etc.; in oral administration, the compound that increases the amount of the GPR17 of the present invention in cell membranes is administered to the patient (as 60 kg body weight) with, e.g., diabetic polyneuropathy normally in a dose of about 0.1 mg to about 100 mg, preferably about 1.0 to about 50 mg, and more preferably about 1.0 to about 20 mg per day. In parenteral administration, the single dose may vary depending on subject to be administered, target organ, conditions, method for administration, etc. and in the form of, e.g., an injectable preparation, the compound that increases the amount of the GPR17 of the present invention in cell membranes is advantageously administered intravenously to the patient (as 60 kg body weight) with, e.g., diabetic polyneuropathy normally in a daily dose of about 0.01 to about 30 mg, preferably about 0.1 to about 20 mg, and more preferably about 0.1 to about 10 mg. For other animal species, the corresponding dose as converted per 60 kg body weight can be administered.

(9) Medicament Comprising the Antibody to the GPR17 of the Present Invention

The neutralizing activity of the antibody to the GPR17 of the present invention means the activity of inactivating the signal transduction function, in which the GPR17 takes part. Thus, when the antibody has the neutralizing activity, the antibody can inactivate signal transduction in which the GPR17 takes part, for example, the GPR17-mediated cell stimulating activities (the activities that promote or suppress arachidonic acid release, acetylcholine release, intracellular $Ca^{2+}$ release, intracellular cAMP production, intracellular cAMP production suppression, intracellular cGMP production, inositol phosphate production, changes in cell membrane potential, phosphorylation of intracellular proteins, activation of c-fos, pH reduction, elevation of gene expression of serum responsive factor, changes in localization of the GPR17 protein in the cell, etc.). Therefore, the neutralizing antibody to the GPR17 of the present invention can be used as an agent for the prevention/treatment of diseases caused by the overexpression of GPR17 or excessive ligands, etc., for example, nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

The preventive/therapeutic agent described above can be manufactured as in the medicament comprising the GPR17 of the present invention described above and provided for use.

(10) Medicament Comprising the Antisense DNA of the Present Invention

The antisense DNA of the present invention can be used as an agent for the prevention/treatment of diseases caused by the overexpression of the GPR17 or excessive ligands, etc., for example, nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

Where the antisense DNA is used, the antisense DNA itself is administered; alternatively, the antisense DNA is inserted into an appropriate vector such as retrovirus vector, adenovirus vector, adenovirus-associated virus vector, etc. and then administered in a conventional manner. The antisense DNA may also be administered as naked, or with auxiliary substances to assist its uptake by gene gun or through a catheter such as a hydrogel catheter. In addition, the antisense DNA may also be used as an oligonucleotide probe for diagnosis to investigate the presence of the DNA of the present invention or the state of its expression in tissues or cells.

As in the antisense polynucleotide described above, the double-stranded RNA containing a part of the RNA encoding the receptor of the present invention (siRNA (small (short) interfering RNA), shRNA (small (short) hairpin RNA), etc. to the receptor of the present invention), the ribozyme containing a part of the RNA encoding the GPR17 and the like can suppress the expression of the GPR17, can suppress the in vivo function of the GPR17 or polynucleotide and are thus useful as low-toxic and safe medicaments, e.g., as agents for the prevention/treatment of, for example, nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.

The double-stranded RNA can be designed based on a sequence of the polynucleotide of the present invention and manufactured by modifications of publicly known methods (e.g., Nature, 411, 494, 2001).

The ribozyme can be designed based on a sequence of the polynucleotide of the present invention and manufactured by modifications of publicly known methods (e.g., TRENDS in Molecular Medicine, 7, 221, 2001). For example, the ribozyme can be manufactured by ligating a publicly known ribozyme to a part of the RNA encoding the receptor of the present invention. A part of the RNA encoding the receptor of the present invention includes a portion in the vicinity of a cleavage site on the RNA of the present invention, which may be cleaved by a publicly known ribozyme (RNA fragment).

Where the double-stranded RNA or ribozyme described above can be used as the agent for the prevention/treatment described above, the RNA or ribozyme can be prepared into pharmaceutical preparations as in the antisense polynucleotide and are provided for administration.

(11) Preparation of animal Bearing the DNA of the Present Invention

The present invention provides a non-human mammal bearing the DNA of the present invention which is exogenous (hereinafter briefly referred to as the exogenous DNA of the present invention) or its variant DNA (sometimes briefly referred to as the exogenous variant DNA of the present invention).

That is, the present invention provides:

[1] A non-human mammal bearing the exogenous DNA of the present invention or its variant DNA;

[2] The mammal according to [1], wherein the non-human mammal is a rodent;

[3] The mammal according to [2], wherein the rodent is mouse or rat; and,

[4] A recombinant vector containing the exogenous DNA of the present invention or its variant DNA and capable of expressing in a mammal; etc.

The non-human mammal bearing the exogenous DNA of the present invention or its variant DNA (hereinafter briefly referred to as the DNA transgenic animal of the present invention) can be produced by transferring a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by means, such as the calcium phosphate method, the electric pulse method, the lipofection method, the agglutination method, the microinjection method, the particle gun method, the DEAE-dextran method, etc. Also, it is possible to transfer the exogenous DNA of the present invention into a somatic cell, a living organ, a tissue cell, or the like by the DNA transfer, and utilize the transformant for cell culture, tissue culture, etc. In addition, these cells may be fused with the above-described germinal cell by a publicly known cell fusion method to prepare the DNA transgenic animal of the present invention.

Examples of the non-human mammals that can be used include bovine, swine, sheep, goat, rabbits, dogs, cats, guinea pigs, hamsters, mice, rats, etc. Above all, preferred are rodents, especially mice (e.g., C57Bl/6 strain, DBA2 strain, etc. for a pure line and for a cross line, B6C3F$_1$ strain, BDF$_1$ strain B6D2F$_1$ strain, BALB/c strain, ICR strain, etc.), rats (Wistar, SD, etc.) or the like, since they are relatively short in ontogeny and life cycle from a standpoint of producing model animals for human disease.

"Mammals" in a recombinant vector that can be expressed in the mammals include the aforesaid non-human mammals and human.

The exogenous DNA of the present invention refers to the DNA of the present invention that is once isolated/extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further includes abnormal DNA.

The abnormal DNA is intended to mean such a DNA that expresses the abnormal the GPR17 of the present invention and exemplified by the DNA that expresses the GPR17 to suppress the functions of normal the GPR17 of the present invention.

The exogenous DNA of the present invention may be any one of those derived from a mammal of the same species as, or a different species from, the mammal as the target animal. In transferring the DNA of the present invention, it is generally advantageous to use the DNA as a DNA construct in which the DNA is ligated downstream a promoter capable of expressing the DNA in the target animal. For example, in the case of transferring the human DNA of the present invention, a DNA transgenic mammal that expresses the DNA of the present invention to a high level, can be prepared by microinjecting a DNA construct (e.g., vector, etc.) of the human DNA of the present invention ligated downstream of various promoters which are capable of expressing the DNA derived from various mammals (e.g., rabbits, dogs, cats, guinea pigs, hamsters, rats, mice, etc.) bearing the DNA of the present invention highly homologous to the human DNA into a fertilized egg of the target non-human mammal, for example, a fertilized egg of a mouse.

As expression vectors for the GPR17 of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), peptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P. myoglobin, troponin C, smooth muscle a actin, preproencephalin A, vasopressin, etc. Among them, cytomegalovirus promoters, human peptide elongation factor 1α (EF-1α) promoters, human and fowl, actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal GPR17 of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of the normal GPR17 obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transferred at the fertilized egg cell stage in a manner such that the DNA is certainly present in all the germinal cells and somatic cells of the target mammal. The fact that the exogenous DNA of the present invention is present in the germinal cells of the animal prepared by DNA transfer means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transferred can be passaged as the DNA-bearing animal under ordinary rearing environment, by confirming that the exogenous DNA is stably retained by crossing.

By transfer of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfer means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygous animals having the transferred DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the GPR17 of the present invention by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the GPR17 of the present invention and the pathological mechanism of the disease associated with the GPR17 of the present invention and to investigate how to treat these diseases. Furthermore, since a mammal transferred with the exogenous normal DNA of the present invention exhibits an increasing symptom of the GPR17 of the present invention, the animal is usable for screening of a drug for the treatment of diseases associated with the GPR17 of the present invention.

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfer of the abnormal DNA of the present invention at the fertilized egg cell stage is preserved to be present in all of the germinal and somatic cells of the target mammal. The fact that the abnormal DNA of the present invention is present in the germinal cells of the animal after DNA transfer means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the GPR17 of the present invention by inhibiting the functions of endogenous normal DNA. Therefore, the animal can be utilized as a pathologic model animal for such a disease. For example, using the abnormal DNA transgenic animal of the present invention, it is possible to elucidate the pathological mechanism of the function inactive type inadaptability to the GPR17 of the present invention and to investigate how to treat the disease.

Specifically, the transgenic animal of the present invention expressing the abnormal DNA at a high level is expected to serve as an experimental model to elucidate the mechanism of the functional inhibition (dominant negative effect) of normal GPR17 by the abnormal GPR17 of the present invention in the function inactive type inadaptability of the GPR17 of the present invention.

A mammal bearing the abnormal exogenous DNA of the present invention has a symptom increasing the GPR17 of the present invention and is thus also expected to serve for screening a candidate drug for the treatment of the function inactive type inadaptability of the GPR17 of the present invention.

Other potential applications of two kinds of the DNA transgenic animals of the present invention described above further include, for example:

(i) Use as a cell source for tissue culture;

(ii) Elucidation of the relation to the GPR17 that is specifically expressed or activated by the GPR17, by direct analysis of DNA or RNA in tissues of the DNA transgenic animal of the present invention or by analysis of the GPR17 tissues expressed by the DNA;

(iii) Research on the function of cells derived from tissues that are usually cultured only with difficulty, using cells in tissues bearing the DNA cultured by a standard tissue culture technique;

(iv) Screening a drug that enhances the functions of cells using the cells described in (iii) above; and, (v) Isolation and purification of the variant GPR17 of the present invention and preparation of an antibody thereto; etc.

Furthermore, clinical conditions of a disease associated with the GPR17 of the present invention, including the function inactive type inadaptability to the GPR17 of the present invention can be determined by using the DNA transgenic animal of the present invention. Also, pathological findings on each organ in a disease model associated with the GPR17 of the present invention can be obtained in more detail, leading to the development of a new method for treatment as well as the research and therapy of any secondary diseases associated with the disease.

It is also possible to obtain a liberated DNA-transferred cell by excising each organ from the DNA transgenic animal of the present invention, mincing the organ and degrading with a proteinase such as trypsin, etc., followed by establishing the line of its culture or cultured cells. Furthermore, the DNA transgenic animal can serve to identify cells capable of producing the GPR17 of the present invention, and to study in association with apoptosis, differentiation or proliferation or on the mechanism of signal transduction in these properties to inspect any abnormality therein. Thus, the DNA transgenic animal can provide an effective research material for the GPR17 of the present invention and for investigation of the function and effect thereof.

To develop a drug for the treatment of diseases associated with the GPR17 of the present invention, including the function inactive type inadaptability to the GPR17 of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the GPR17 of the present invention, using the DNA transgenic animal of the present invention or a vector capable of expressing the exogenous DNA of the present invention.

(12) Knockout Animal

The present invention provides a non-human mammalian embryonic stem cell bearing the DNA of the present invention inactivated and a non-human mammal deficient in expressing the DNA of the present invention.

Thus, the present invention provides:

[1] A non-human mammalian embryonic stem cell in which the DNA of the present invention is inactivated;

[2] The embryonic stem cell according to [1], wherein the DNA is inactivated by introducing a reporter gene (e.g., β-galactosidase gene derived from *Escherichia coli*);

[3] The embryonic stem cell according to [1], which is resistant to neomycin;

[4] The embryonic stem cell according to [1], wherein the non-human mammal is a rodent;

[5] The embryonic stem cell according to [4], wherein the rodent is mouse;

[6] A non-human mammal deficient in expressing the DNA of the present invention, wherein the DNA is inactivated;

[7] The non-human mammal according to [6], wherein the DNA is inactivated by inserting a reporter gene (e.g., β-galactosidase derived from *Escherichia coli*) therein and the reporter gene is capable of being expressed under control of a promoter for the DNA of the present invention;

[8] The non-human mammal according to [6], which is a rodent;

[9] The non-human mammal according to [8], wherein the rodent is mouse; and,

[10] An increased gene expression of serum responsive factor or a change in localization of the GPR17 in the cell protein of the compound or its salt that promotes or inhibits (preferably inhibits) the promoter activity to the DNA of the present invention, which comprises administering a test compound to the mammal of

[7] and detecting expression of the reporter gene.

The non-human mammal embryonic stem cell in which the DNA of the present invention is inactivated refers to a non-human mammal embryonic stem cell (hereinafter merely referred to as ES cell) that suppresses the ability of the non-human mammal to express the DNA by artificially mutating the DNA of the present invention, or the DNA has no substantial ability to express the GPR17 of the present invention (hereinafter sometimes referred to as the knockout DNA of the present invention) by substantially inactivating the activities of the GPR17 of the present invention encoded by the DNA.

As the non-human mammal, the same examples as given above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a drug resistant gene such as a neomycin resistant gene or a hygromycin resistant gene, or a reporter gene such as lacZ (β-galactosidase gene) or cat (chloramphenicol acetyltransferase gene), etc. into its exon region thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter briefly referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, for the purpose of obtaining a pure line of ES cells with the clear immunological genetic background instead of the ES cells of the 129 strain and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocysts at 3.5 days after fertilization are commonly used, and embryos are preferably collected at the 8-cell stage, after culturing until the blastocyst stage, the embryos are used to efficiently obtain a large number of early stage embryos. Although the ES cells used may be of either sex, male ES cells are generally more convenient for generation of a germ cell line chimera. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, whereas karyotype analysis requires about $10^6$ cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, parietal and visceral muscles, cardiac muscle or the like [M. J. Evans and M. H. Kaufman, Nature, 292, 154, 1981; G. R. Martin, Proc. Natl. Acad. Sci. U.S.A, 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for studying the GPR17 of the present invention in vitro or the GPR17 of the present invention cytologically.

The non-human mammal deficient in expression of the DNA of the present invention can be identified from a normal animal by measuring the mRNA level in the subject animal by a publicly known method, and indirectly comparing the degrees of expression.

As the non-human mammal, the same examples supra apply.

With respect to the non-human mammal deficient in expression of the DNA of the present invention, the DNA of the present invention can be made knockout by transferring a targeting vector, prepared as described above, to mouse embryonic stem cells or mouse oocytes, and conducting homologous recombination in which a targeting vector DNA sequence, wherein the DNA of the present invention is inactivated by the transfer, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention. When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the GPR17 of the present invention. The individuals deficient in homozygous expression of the GPR17 of the present invention can be obtained from offspring of the intercross between those deficient in heterozygous expression of the GPR17 of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is rendered knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygous animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention. Since the non-human mammal, in which the DNA of the present invention is inactivated, lacks various biological activities derived from the GPR17 of the present invention, such an animal can be a disease model suspected of inactivated biological activities of the GPR17 of the present invention and thus, offers an effective study to investigate the causes for and therapy for these diseases.

(12a) Method of Screening a Compound Having Therapeutic/Preventive Effects on Diseases Caused by Deficiency, Damages, etc. of the DNA of the Present Invention The non-human mammal deficient in expression of the DNA of the present invention can be employed for screening of a compound having therapeutic/preventive effects on diseases caused by deficiency, damages, etc. of the DNA of the present invention.

That is, the present invention provides a method of screening a compound or its salt having a therapeutic/preventive effect on diseases caused by deficiency, damages, etc. of the DNA of the present invention, which comprises administering a test compound to a non-human mammal deficient in expression of the DNA of the present invention and, observing and measuring a change occurred in the animal. As the non-human mammal deficient in expression of the DNA of the present invention, which can be employed for the screening methods, the same examples as given hereinabove apply.

Examples of the test compounds include peptides, proteins, antibodies, non-peptide compounds, synthetic compounds, fermentation products, cell extracts, plant extracts, animal tissue extracts, plasma, etc. These compounds may be novel compounds or publicly known compounds. The test compounds may form salts and as salts of the test compounds, there are, for example, physiologically acceptable metal salts, ammonium salts, salts with organic bases, salts with inorganic acids, salts with organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/preventive effects of the test compound. For treating an animal to be tested with a test compound, for example, oral administration, intravenous injection, etc. are applied, and the treatment can be appropriately selected depending on conditions of the test animal, properties of the test compound, etc. Furthermore, a dose of the test compound to be administered can be appropriately selected depending on the administration methods, nature of the test compound, etc.

When a test compound is administered to a test animal in the screening methods and blood inflammation symptom of the test animal improved by at least about 10%, preferably at least 30%, more preferably at least about 50%, the test compound can be selected to be a compound having a therapeutic/preventive effect on the diseases described above.

The compound obtained using the above screening methods is a compound selected from the test compounds described above and can be used as a medicament, e.g., as a safe and low toxic agent for the prevention/treatment of diseases caused by deficiencies, damages, etc. of the GPR17 of the present invention, for example, neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), etc.), or the like. In addition, compounds derived from the compounds obtained by the screening described above can be used as well.

The compounds obtained by the screening methods may form salts and as salts of the compounds, there are, for example, physiologically acceptable metal salts, ammonium salts, salts with organic bases, salts with inorganic acids, salts with organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc.

The medicament comprising the compound or salts thereof, which are obtained by the above screening methods, can be manufactured in a manner similar to the method for preparing the medicament comprising the compound that alters the binding properties of the GPR17 of the present invention to the ligand peptide described above.

The pharmaceutical preparation thus obtained is safe and low toxic, and can be administered to human or mammal (e.g., rat, mouse, guinea pig, rabbit, sheep, swine, bovine, horse, cat, dog, monkey, etc.).

The dose of the compound or its salt may vary depending on target disease, subject to be administered, route for administration, etc.; in oral administration, the compound is administered to the patient (as 60 kg body weight) with, e.g., diabetic polyneuropathy normally in a dose of about 0.1 mg to about 100 mg, preferably about 1.0 to about 50 mg, and more preferably about 1.0 to about 20 mg per day. In parenteral administration, the single dose may vary depending on subject to be administered, target disease, etc. and in the form of, e.g., an injectable preparation, it is advantageous to administer the compound intravenously to the patient (as 60 kg body weight) with, e.g., diabetic polyneuropathy normally in a daily dose of about 0.01 to about 30 mg, preferably about 0.1 to about 20 mg, and more preferably about 0.1 to about 10 mg. For other animal species, the corresponding dose as converted per 60 kg body weight can be administered.

(12b) Method of Screening a Compound that Promotes or Inhibits the Activity of a Promoter to the DNA of the Present Invention The present invention provides a method of screening a compound or its salt that promotes or inhibits the activity of a promoter to the DNA of the present invention, which comprises administering a test compound to a non-human mammal deficient in expression of the DNA of the present invention and detecting the expression of the reporter gene.

In the screening methods described above, an animal in which the DNA of the present invention is inactivated by introducing a reporter gene and the reporter gene is expressed under control of a promoter to the DNA of the present invention is used as the non-human mammal deficient in expression of the DNA of the present invention, which is selected from the aforesaid non-human mammals deficient in expression of the DNA of the present invention.

The same examples of the test compounds as described above apply as well.

As the reporter gene, the same specific examples apply to this screening method. Preferably, there are used β-galactosidase (lacZ), soluble alkaline phosphatase gene, luciferase gene and the like. Since the reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the GPR17 of the present invention is substituted with, e.g., β-galactosidase gene (lacZ) derived from *Escherichia coli*, β-galactosidase is expressed in a tissue where the GPR17 of the present invention should originally be expressed, instead of the GPR17 of the present invention. Thus, the expression state of the GPR17 of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the GPR17 of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or its salt obtained using the screening methods described above is a compound selected from the test compounds described above, which promotes or inhibits the activity of a promoter to the DNA of the present invention. The compounds obtained by the screening methods may form salts and as salts of the compounds, there are, for example, physiologically acceptable metal salts, ammonium salts, salts with organic bases, salts with inorganic bases, salts with basic or acidic amino acids, etc. Preferred examples of the metal salts include salts with alkali metal salts such as sodium salts, potassium salts, etc.; alkaline earth metal salts such as calcium salts, magnesium salts, barium salts, etc.; aluminum salts, etc. Preferred examples of the salts with organic bases include trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc. and preferred examples of the salts with acidic amino acids include salts with aspartic acid, glutamic acid, etc.

The compound or its salt that promotes the activity of a promoter to the DNA of the present invention can promote the expression of the GPR17 of the present invention and promote the function of the GPR17, and can be used as a medicament, e.g., as an agent for the prevention/treatment of diseases associated with the dysfunction of the GPR17 of the present invention. Specifically, the compound can be used as a low-toxic and safe medicament, e.g., as an agent for the prevention/treatment of neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.).

The compound or its salt that inhibits the activity of a promoter to the DNA of the present invention is useful as a medicament, e.g., as an agent for the prevention/treatment of, for example, nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.).

In addition, compounds derived from the compounds obtained by the screening described above can be used as well.

The medicament comprising the compound or its salt obtained by the above screening methods can be manufactured as in the medicament comprising the compound that alters the binding properties of the GPR17 of the present invention or its salt to the ligand peptide described above.

The pharmaceutical preparation thus obtained is safe and low toxic, and can be administered to, for example, human or other mammal (e.g., rat, mouse, guinea pig, rabbit, sheep, swine, bovine, horse, cat, dog, monkey, etc.).

The dose of the compound or its salt may vary depending on target disease, subject to be administered, route for administration, etc.; in oral administration, the compound that promotes the activity of a promoter to the DNA of the present invention is administered to the patient (as 60 kg body weight) with a neurogenic disorder normally in a dose of about 0.1 mg to about 100 mg, preferably about 1.0 to about 50 mg, and more preferably about 1.0 to about 20 mg per day. In parenteral administration, the single dose may vary depending on subject to be administered, target disease, etc. and in the form of, e.g., an injectable preparation, the compound that promotes the activity of a promoter to the DNA of the present invention is advantageously administered intravenously to the patient (as 60 kg body weight) with a neurogenic disorder normally in a daily dose of about 0.01 to about 30 mg, preferably about 0.1 to about 20 mg, and more preferably about 0.1 to about 10 mg. For other animal species, the corresponding dose as converted per 60 kg body weight can be administered.

As stated above, the non-human mammal deficient in expression of the DNA of the present invention is extremely useful for screening the compound or its salt that promotes or inhibits the activity of a promoter to the DNA of the present invention and can greatly contribute to elucidation of causes for various diseases derived from deficiency in expression of the DNA of the present invention and for the development of preventive/therapeutic drugs for these diseases.

Also, a so-called transgenic animal (gene transferred animal) can be prepared by using a DNA containing the promoter region of the GPR17 of the present invention, ligating genes encoding various proteins at the downstream and injecting the same into oocyte of an animal. It is thus possible to synthesize the GPR17 specifically and study its activity in vivo. When an appropriate reporter gene is ligated to the promoter site described above and a cell line that expresses the gene is established, the resulting system can be utilized as the search system for a low molecular compound having the action of specifically promoting or inhibiting the in vivo productivity of the GPR17 of the present invention itself.

In the specification and drawings, the codes of bases, amino acids, etc. are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |
| * | corresponding to termination codon |
| Me | methyl group |
| Et | ethyl group |
| Bu | butyl group |
| Ph | phenyl group |
| TC | thiazolidine-4(R)-carboxamido group |

Substituents, protecting groups and reagents frequently used in this specification are presented as the codes below.

| | |
|---|---|
| Tos | p-toluenesulfonyl |
| CHO | formyl |
| Bzl | benzyl |
| Cl$_2$—Bzl | 2,6-dichlorobenzyl |
| Bom | benzyloxymethyl |
| Z | benzyloxycarbonyl |
| Cl—Z | 2-chlorobenzyloxycarbonyl |
| Br—Z | 2-bromobenzyl oxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dicyclohexylcarbodiimide |

The sequence identification numbers in the sequence listing of the specification indicates the following sequence, respectively.

[SEQ ID NO: 1]

This shows the amino acid sequence of the human-derived GPR17 of the present invention.

[SEQ ID NO: 2]

This shows the base sequence of cDNA encoding the human-derived GPR17 of the present invention.

[SEQ ID NO: 3]

This shows the base sequence of the primer used in EXAMPLE 4.

[SEQ ID NO: 4]

This shows the base sequence of the primer used in EXAMPLE 4.

[SEQ ID NO: 5]

This shows the base sequence of the probe used in EXAMPLE 4.

EXAMPLES

Hereinafter, the present invention will be described below in more detail with reference to EXAMPLES but is not deemed to limit the scope of the present invention. Gene using Escherichia coli was carried out by the methods described in Molecular Cloning.

Example 1

Transient Expression of G Protein-Coupled Receptor Protein Expression Plasmid and Reporter Plasmid in Host Cells (HeLa)

First, cDNA encoding the G protein-coupled receptor protein, GPR17 (SEQ ID NO: 1) was inserted into pAKKO-111H (the same plasmid vector as pAKKO-1.111H described in Biochem. Biophys. Acta, Hinuma, S. et al., 1219, 251-259, 1994). Using the prepared expression plasmid for animal cells, Escherichia coli JM109 was transfected and the colonies obtained were isolated and cultured. Thereafter, large scale plasmid preparation was carried out using QIAGEN Plasmid Maxi Kit (Qiagen). Furthermore, a reporter plasmid of the pSRE-Luc (Invitrogen) ligated with a luciferase gene as a reporter at the downstream of serum response element (SRE), and expression vector plasmids for human GαoA, human Gβ1 and human Gγ2, which are a kind of G proteins, were prepared in a similar manner.

HeLa cells as host cells for transfecting the G protein-coupled receptor protein expression plasmid and the reporter plasmid were plated on a 384-well assay plate (COSTAR 3704) at 4000 cells/well in a culture volume of 25 µl, followed by incubation overnight. The medium used was DMEM (Invitrogen) supplemented with 10% fetal calf serum and 1% MEM non-essential amino acids solution (DMEM/NEAA).

Each plasmid was diluted to a concentration of 240 ng/µl, and added to 240 µl of Opti-MEM-I (Invitrogen) in a proportion of 1 µl of the expression plasmid for G protein-coupled receptor protein, or, for control, plasmid for expression vector pAKKO-111H free of DNA encoding the receptor protein in place of an expression plasmid of the receptor, 9 µl of the reporter plasmid and 1 µl each of the G protein-coupled receptor protein expression plasmid of GαoA, Gβ1 or Gγ2. The mixture was mixed with also 240 µl of Opti-MEM-I added with 10 µl of Lipofectamine™ 2000 Reagent (Invitrogen) in equal volumes to form the liposome and plasmid complex, in accordance with the procedure instructed in the manual attached. These mixtures were added to the culture solution of HeLa cells in 5 µl each/well to transfect the plasmid, followed by incubation overnight at 37° C. in 5% $CO_2$.

Example 2

Detection of Ligand Activity by Reporter Assay

The HeLa cells prepared in EXAMPLE 1 were washed twice with fetal calf serum-free DMEM/NEAA (assay medium) and then cultured at 37° C. under 5% $CO_2$ for 2 hours. After the cells were further washed once with an assay buffer, a solution of 5-aminolevulinic acid (ALA) in 0.05% CHAPS-containing assay medium was exposed to the cells in each well. After a sample was added, incubation was conducted at 37° C. under 5% $CO_2$ for 4 hours to induce promotion of the transcription/translation of the reporter gene derived from intracellular signal transduction caused by the agonist activity of a ligand mediated by the receptor. After the incubation was completed, the assay buffer in each well was removed and 8 µl each of PicaGene LT 2.0 (Toyo Ink Mfg. Co., Ltd.) as a substrate for assaying the luciferase activity was added to the well. After the cells were lysed and thoroughly mixed with the substrate, the chemiluminescence level corresponding to the expression induction level of the reporter gene in each well was measured on the plate reader (EnVision™, Perkin-Elmer).

As a result, an increased luciferase activity was noted in the GPR17-expressed cells by the addition of ALA (200 µM), as shown in TABLE 1. On the other hand, any significant increase of the activity was not detected in the pAKKO-111H transfected cells for control, even when ALA (200 µM) was added.

TABLE 1

Increased Luciferase Activity (cps) by ALA in GPR17-Expressed Cells

| ALA Level (µM) | GPR17 | pAKKO-111H (control) |
|---|---|---|
| 0 | 1536 | 1180 |
| 200 | 6707 | 1376 |

Example 3

Movement of GPR17-GFP Fusion Protein Expressed in CHO Cells into Cells by Addition of 5-Aminolevulinic Acid An expression plasmid was constructed to express a fused protein of Green Fluorescent Protein (GFP) cDNA isolated from jelly fish Auquorea victoria, fused to GPR17 at the C-terminus to fit the translation frame. In this case, a fragment excised from GFP expression vector pQBI25 (Takara Shuzo Co., Ltd.) was used as GFP cDNA. In GPR17, its termination codon was modified by PCR to recognition sequence with restriction enzyme NheI, and the GFP fragment was ligated thereto, which was inserted into the expression vector pAKKO-111H described in EXAMPLE 1. Using the thus obtained plasmid of the GPR17 and GFP fusion protein (hereinafter GPR17-GFP fusion protein) expression vector, GPR17-GFP expression CHO (CHO-GPR17-GFP) capable of stably expressing GPR17-GFP was produced by a publicly known method. The CHO cells were plated on a Lab-TekII cover glass chamber with 8 chambers (Nalgen Nunc, Inc.). After incubation overnight at 37° C. in 5% $CO_2$, the fluorescent images of GFP were observed with a confocal microscope (Leica, Inc.). Then, the medium was replaced with DMEM (Dulbecco's Modified Eagle Medium) (GIBCO BRL) containing 100 µM 5-aminolevulinic acid. The reaction was conducted under the conditions of 37° C. and 5% $CO_2$ for 45 minutes, whereby changes in the fluorescent images of GFP were observed with a confocal microscope.

As a result, it was found that the GPR17-GFP fusion protein detected mainly on the cell membrane prior to the addition of 5-aminolevulinic acid moved in part to the cytoplasm. This indicates that GPR17 moved to the cytoplasm in response to 5-aminolevulinic acid, namely, 5-aminolevulinic acid acted on GPR17.

Example 4

Expression Distribution of Human GPR17 mRNA

For quantification of the expression level of mRNA, ABI PRISM7700 SequenceDetector (Applied Biosystems) was used. Primers [5'-GTCTCACCGGCTTCCTCTTCT-3' (SEQ ID NO: 3), 5'-AAACGGTCGGCGCTGAT-3' (SEQ ID NO: 4)] and probe [5'-CCTCAACATGTACGCCAGCATCTACT-TCCT-3' (SEQ ID NO: 5)] used for the expression level quantification were designed based on the base sequence of human GPR17 (SEQ ID NO: 2) using software PrimerExpress (Applied Biosystems) exclusively for ABI PRISM 7700 SequenceDetector. The cDNA for a template was synthesized from 1 µg of the total RNA (Clontech) derived from various human tissues by reverse transcription using random primers, which was provided for use. For the reverse transcription, SuperScript II (GIBCO BRL) reverse transcriptase was used. The reaction was performed in accordance with the manual attached. The reaction solution for ABI PRISM 7700 SequenceDetector consisted of 12.5 µl of TaqMan Universal PCR Master Mix (Applied Biosystems), 0.9 µM each of the primers, 0.25 µM of the probe and the cDNA solution, to which distilled water was added to make 25 µl. The reaction for ABI PRISM 7700 SequenceDetector was carried out at 50° C. for 2 minutes and 95° C. for 10 minutes, followed by repeating 40 times a cycle set to include 95° C. for 15 seconds and 60° C. for 1 minute. Expression distribution of the mRNA in various human tissues is shown in FIG. 1. High expression level was detected in the central nervous system including the spinal cord.

Example 5

Suppression of Intracellular cAMP Level Increased After Forskolin Addition in GPR17-Expressed CHO Cells by ALA Using the GPR17 expression vector described in EXAMPLE 1, GPR17-expressed CHO cells capable of stably expressing GPR17 was produced by a publicly known method. The GPR17-expressed CHO cells was incubated overnight and then washed with an assay medium (HBBBS supplemented with 0.1% bovine serum albumin and 0.2 mM IBMX, followed by incubation at 37° C. for 30 minutes under 5% $CO_2$ conditions. ALA diluted with the assay medium in various concentrations and forskolin were added thereto in 2 µM, followed by incubation at 37° C. for 30 minutes under 5% $CO_2$ conditions. The culture supernatant was discarded and the intracellular cAMP level was determined on a plate reader (EnVision, PerkinElmer), following the protocol of cAMP Screen Kit (Applied Biosystems).

Figure 2:
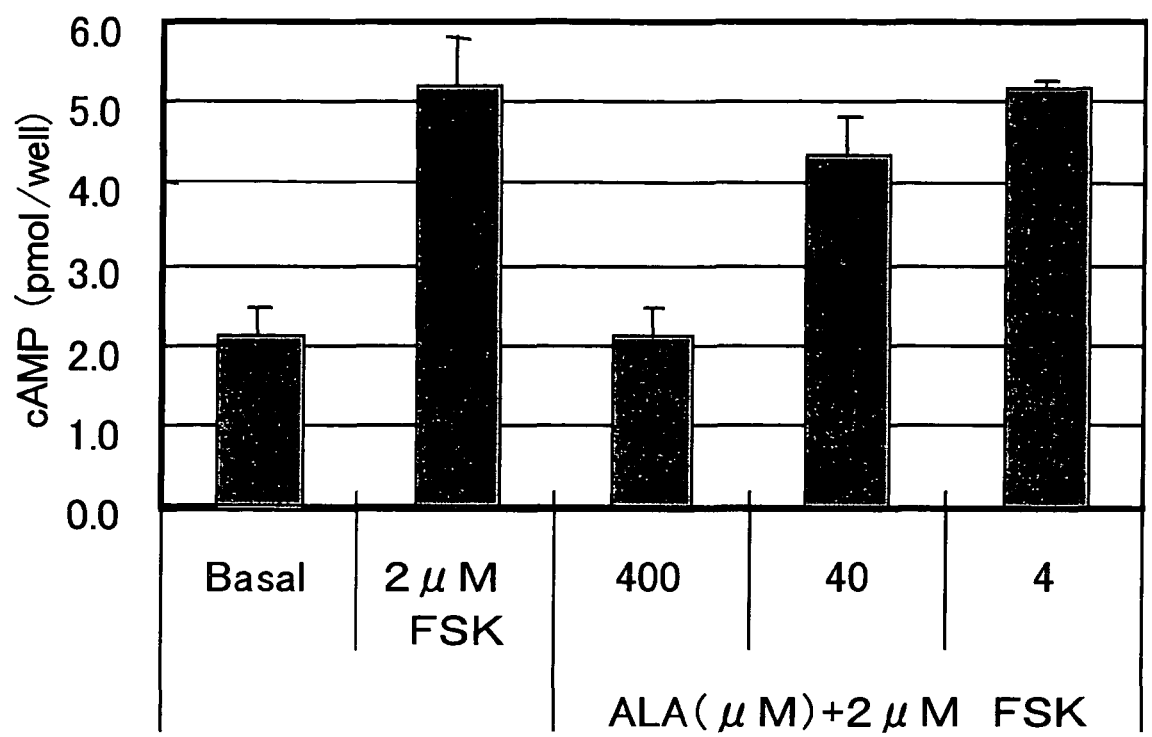
FIG. 2 shows dose-dependency of the ligand activity of ALA specific to the GPR17 receptor-expressed CHO cells, depending upon intracellular cAMP level. Incubation was carried out under 2 µM of forskolin added (FSK) and under ALA in the concentrations given in the figure in the presence of forskolin, and the intracellular cAMP levels were compared to the level without forskolin stimulation (Basal).

As a result, dose-dependent and specific decrease of the intracellular cAMP level by ALA, which had been increased by forskolin addition, was detected specifically in the CHO cells introduced with the human GPR17 gene (FIG. 2).

Experiment 6

Pain Relief Action of 5-Aminolevulinic Acid

Figure 3:
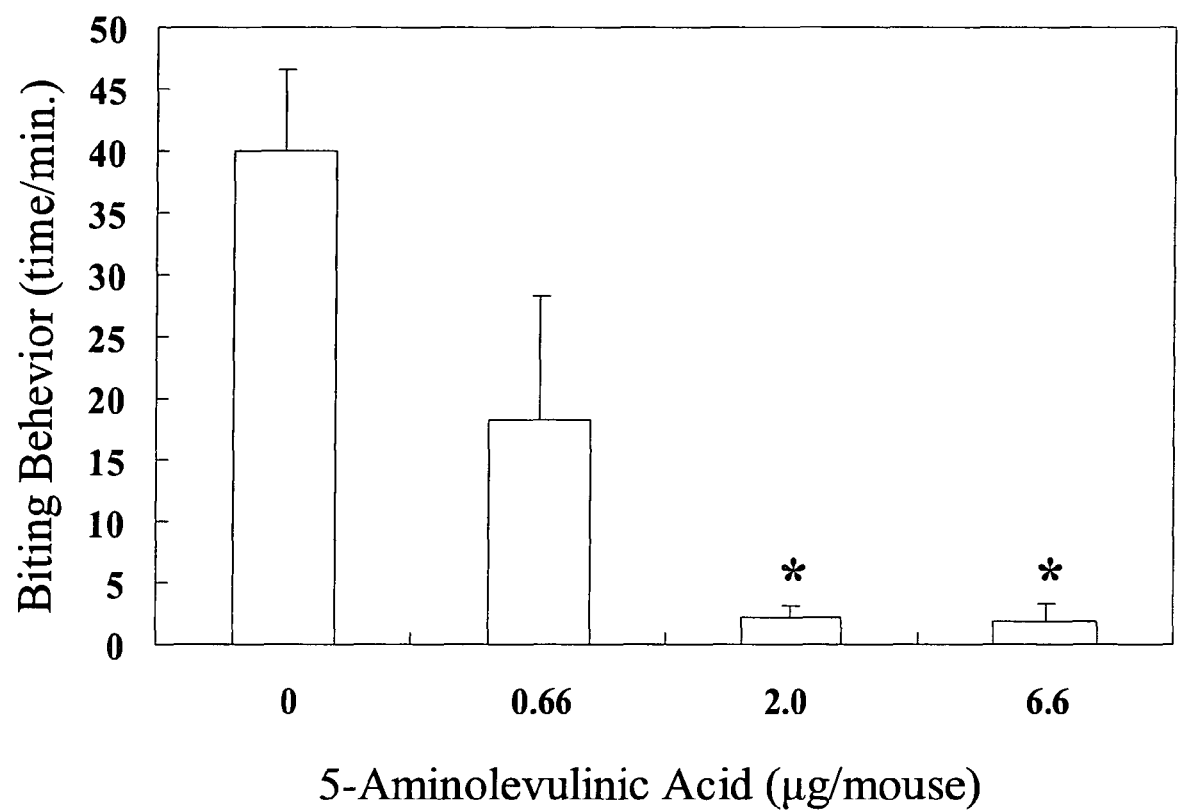
FIG. 3 shows the results obtained by assessment of biting response when ALA and Substance P were intrathecally given to mice. The numerical values designate mean±standard error (n=6). Symbol * shows that the effect of ALA for suppressing the pain response is significant when compared to the group administered with Substance P alone (group without administration of ALA) ($p<0.05$).

In order to examine effects of 5-aminolevulic acid (ALA) on pain, ALA was mixed with substance P (SP) and the mixture was intrathecally administered. Male ICR mice of 5 weeks age for intrathecal administration received incision on the dorsal tail and habituated at least for an hour. Thereafter, SP (10 µg) alone or a mixture of SP (10 µg) and ALA was intrathecally administered to the mice (5 µL/mouse) between the L5 and L6 level of the spinal cord, under no anesthesia. Immediately after administration, the number of times that the mice bit the underbody mutually was counted for one minute and the number was made an indicator of false pain response by SP. As a result, ALA showed a significant suppression effect on the SP-induced biting response (pain response) by administration of 0.66, 2.0 and 6.6 µg/mouse, as shown in FIG. 3. When ALA alone was intrathecally given, no change was observed in the behavior of mice.

Example 7

Detection of Ligand Activity of Porphobilinogen (PBG) on GPR17 by Reporter Assay The ligand activity of PBG on human GPR17 expression cells was examined in the same manner as in EXAMPLE 2. As a result, an increased luciferase activity was detected in the GPR17 expression cells by the addition of 1000 µM of PBG. On the other hand, PBG did not show any significant increase in the GPR40 expression cells used for control.

TABLE 2

| Increased luciferase activity (cps) in the GPR17 expression cells by PBG | | |
|---|---|---|
| Concentration of PBG (µM) | GPR17 | GPR40 (control) |
| 0 | 4409 | 4729 |
| 1000 | 37999 | 3769 |

INDUSTRIAL APPLICABILITY

The compound or its salt that alters the binding properties of the receptor protein comprising the same or substantially the same amino acid sequence as the amino acid sequence represented by SEQ ID NO: 1, a partial peptide thereof, or a salt thereof, to the ligand or a salt thereof; the compound or its salt that promotes the activities of the receptor protein; the compound or its salt that promotes the binding properties of the receptor protein to the ligand; the receptor protein; etc. can be used as an agent for the prevention/treatment of, for example, neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), or the like.

The compound or its salt that inhibits the activities of the receptor protein, the antibody to the receptor protein, the antisense nucleotide for the receptor protein, etc. can be used as an agent for the prevention/treatment of, for example, nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), or the like.

The receptor protein, its partial peptide, or a salt thereof and the ligand or a salt thereof are useful for screening agents for the prevention/treatment of neurogenic pains (e.g., diabetic polyneuropathy, entrapment (compression) peripheral neuropathy, phantom limb pain, thalamic pain, postherpetic neuralgia, atypical facial pain after tooth extraction, etc., spinal cord injury, trigeminal neuralgia, cancer pain, etc.), nervous system disorders (e.g., Huntington's disease, Parkinson's disease, striatonigral degeneration, GM1 gangliosidosis, Wilson's disease, schizophrenia, depression, anxiety, attention deficit hyperactivity disorders (ADHD), Alzheimer's disease, multiple sclerosis, mood disorders, anxiety disorders, disturbance of thinking and volition, bipolar affective disorders, sleep and awakening disorders, myopathy (muscle disorders), obesity, urinary incontinence, epilepsy, spasm, etc.), or the like.

The invention claimed is:

1. A method of screening a compound or its salt that alters the binding property of a G protein-coupled receptor protein comprising an amino acid sequence having at least 90% homology to the amino acid sequence of SEQ ID NO: 1 or a salt thereof, to a ligand or a salt thereof, which comprises:

comparing the binding amount of the ligand or a salt thereof to the receptor protein between the following two cases: (i) the case wherein the receptor protein is brought in contact with the ligand or a salt thereof; and (ii) the case wherein the receptor protein is brought in contact with the ligand or a salt thereof and a test compound, and identifying whether the test compound alters the binding property of the receptor protein to the ligand or a salt thereof, wherein the ligand is 5-aminolevulinic acid or porphobilinogen.

2. A method of screening an agonist or antagonist of a G protein-coupled receptor protein comprising an amino acid sequence having at least 90% homology to the amino acid sequence of SEQ ID NO: 1 or a salt thereof, which comprises:

comparing the cell stimulating activities between the following two cases: (i) the case wherein the receptor protein is brought in contact with a ligand to the receptor protein; and (ii) the case wherein the receptor protein is brought in contact with the ligand or a salt thereof and a test compound, and identifying whether the test compound is an agonist or antagonist, wherein the ligand is 5-aminolevulinic acid or porphobilinogen.

3. A method of screening an agonist or antagonist of a G protein-coupled receptor protein comprising an amino acid sequence having at least 90% homology to the amino acid sequence of SEQ ID NO: 1 or a salt thereof, which comprises:

comparing the signal transduction between (i) the case where a ligand or a salt thereof is brought in contact with a cell containing said receptor protein and (ii) the case where a test compound is brought in contact with a cell containing said receptor protein, in the presence of a ligand or a salt thereof, and identifying whether the test compound is an agonist or antagonist, wherein the ligand is 5-aminolevulinic acid or porphobilinogen.

* * * * *